(12) United States Patent
Gunn et al.

(10) Patent No.: US 12,390,449 B2
(45) Date of Patent: *Aug. 19, 2025

(54) SUBSTITUTED 2-AMINOBENZIMIDAZOLES ANALOGS AS ANTIBIOFILM AGENTS

(71) Applicants: Ohio State Innovation Foundation, Columbus, OH (US); North Carolina State University, Raleigh, NC (US)

(72) Inventors: John Gunn, Columbus, OH (US); Laura Kuo, Columbus, OH (US); Christian Melander, Raleigh, NC (US); William M. Huggins, Raleigh, NC (US)

(73) Assignees: Ohio State Innovation Foundation, Columbus, OH (US); North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/545,458

(22) Filed: Dec. 19, 2023

(65) Prior Publication Data

US 2024/0156788 A1  May 16, 2024

Related U.S. Application Data

(60) Continuation of application No. 17/841,938, filed on Jun. 16, 2022, now Pat. No. 11,883,384, which is a division of application No. 17/044,517, filed as application No. PCT/US2019/025683 on Apr. 3, 2019, now abandoned.

(60) Provisional application No. 62/651,829, filed on Apr. 3, 2018.

(51) Int. Cl.
*A61K 31/4184* (2006.01)

(52) U.S. Cl.
CPC .............. *A61K 31/4184* (2013.01)

(58) Field of Classification Search
CPC .................................. A61K 31/4184
See application file for complete search history.

(56) References Cited

U.S. PATENT DOCUMENTS

| 4,011,236 | A | 3/1977 | Grier |
| 9,221,765 | B2 | 12/2015 | Melander et al. |

FOREIGN PATENT DOCUMENTS

| WO | 20180035018 A1 | 2/2018 |

OTHER PUBLICATIONS

Huigens R W et al: "The chemical synthesis and antibiotic activity of a diverse library of 2-aminobenzimidazole small molecules against MRSA and multidrug-resistant A. baumannii", Bioorganic, Elsevier, Amsterdam, NL, vol. 18, No. 2, Jan. 15, 2010 (Jan. 15, 2010), pp. 663-674, XP026835897, ISSN: 0968-0896 [retrieved on Dec. 6, 2009].

(Continued)

*Primary Examiner* — Kamal A Saeed
(74) *Attorney, Agent, or Firm* — Thomas | Horstemeyer, LLP

(57) ABSTRACT

In one aspect, the disclosure relates to compositions and methods for dispersing exiting *Salmonella* biofilms and inhibiting formation of *Salmonella* biofilms. In various aspects, the disclosed compositions can be used in methods of treating a persistent *Salmonella* infection, including an asymptomatic infection. Such infections can colonize a variety of tissues, including the gall-bladder. Also disclosed are methods of treating typhoid fever. Also disclosed are methods for mitigating or preventing secondary outbreaks of typhoid fever by treating asymptomatic subjects who had been symptomatic for typhoid fever at a previous time. This abstract is intended as a scanning tool for purposes of searching in the particular art and is not intended to be limiting of the present disclosure.

20 Claims, 11 Drawing Sheets

(56) References Cited

OTHER PUBLICATIONS

T. Vu Nguyen et al: "The Discovery of 2-Aminobenzimidazoles That Sensitize Mycobacterium smegmatis and M. tuberculosis to beta-Lactam Antibiotics in a Pattern Distinct from beta-Lactamase Inhibitors", Angewandte Chemie International Edition, vol. 56, No. 14, Mar. 27, 2017 (Mar. 27, 2017), pp. 3940-3944, XP055718404, ISSN: 1433-7851, DOI: 10.1002/anie.201612006.

Erick A. Lindsey et al: "The discovery of N-1 substituted 2-aminobenzimidazoles as zinc-dependent S. aureus biofilm inhibitors", MEDCHEMCOMM, vol. 3, No. 11, Jan. 1, 2012 (Jan. 1, 2012), p. 1462, XP055207160, ISSN: 2040-2503, DOI: 10.1039/c2md20244a.

Huggins William M. et al: "2-Aminobenzimidazoles as antibiofilm agents against Salmonella enterica serovar Typhimurium", MEDCHEMCOMM, vol. 9, No. 9, Aug. 2, 2018 (Aug. 2, 2018), pp. 1547-1552, XP55858056, United Kingdom ISSN: 2040-2503, DOI: 10.1039/C8MD000298C.

Roberta J. Worthington et al: "Small molecule control of bacterial biofilms", Organic & Biomolecular Chemistry, vol. 10, No. 37, Jan. 1, 2012 (Jan. 1, 2012), p. 7457, XP055635047, ISSN: 1477-0520, DOI: 10.1039/c20b25835h.

Liu Chang et al: "A New Small Molecule Specifically Inhibits the Cariogenic Bacterium *Streptococcus mutans* in Multispecies Biofilms", Antimicrobial Agents and Chemotherapy, vol. 55, No. 6, Mar. 14, 2011 (Mar. 14, 2011), pp. 2679-2687, XP055858095, Us ISSN: 0066-4804, DOI: 10.1128/AAC.01496-10.

Musk Dinty J.: "Zinc Fingered: New Compounds that Thwart Gram-Positive Biofilm Formation by Sequestering Zinc", CHEMBIOCHEM, vol. 11, No. 6, Feb. 28, 2010 (Feb. 28, 2010), pp. 758-760, XP055858101, ISSN: 1439-4227, DOI: 10.1002/chic.200900691.

Extended European Search Report Application No. 19781899.0-1109 mailed Nov. 22, 2021.

International Search Report issued for PCT/US2019/025683 mailed Aug. 2, 2019.

PUBCHEM-CID: 20430845 Create Date: Dec. 5, 2007 (Dec. 5, 2007) pp. 1-8; p. 2, structure.

10a-t

SUBSTITUTED 2-AMINOBENZIMIDAZOLES ANALOGS AS ANTIBIOFILM AGENTS

CROSS-REFERENCE TO RELATED APPLICATIONS

This application is a continuation application of U.S. Nonprovisional application Ser. No. 17/841,938, filed on Jun. 16, 2022, which is a divisional application of U.S. Nonprovisional application Ser. No. 17/044,517, filed on Oct. 1, 2020, which is a National Stage of International Application No. PCT/US2019/025683, filed Apr. 3, 2019, which claims the benefit of U.S. Provisional Application No. 62/651,829, filed on Apr. 3, 2018, which is incorporated herein by reference in its entirety.

BACKGROUND

A "biofilm" is a well known phenomenon and may be defined as a population of prokaryotic cells growing on a surface and enclosed in a self-produced matrix of extracellular polymeric material, which mediates adhesion of the cells to each other and to surfaces. Biofilms are not simply passive assemblages of cells that are stuck to surfaces, but are structurally and dynamically complex biological systems. As compared with cells that are planktonic in nature, bacteria growing in biofilms exhibit a different phenotype with respect to growth rate and gene transcription.

Biofilms may be involved in a significant percentage of human microbial infections (Potera C. Forging a link between biofilms and disease. Science 1999; 283:1837-8). Parsek and Singh proposed four criteria for defining a biofilm etiology of an infection: the pathogenic bacteria are surface associated or adherent to a substratum; direct examination reveals bacteria in clusters, encased in a matrix of bacterial or host constituents; the infection is localized; and the infection is resistant to antibiotic therapy despite the antibiotic sensitivity of the constituent planktonic organisms (Parsek M R, Singh P K. Bacterial biofilms: an emerging link to disease pathogenesis. Annu Rev Microbiol 2003; 57:677-701).

Biofilm infections can be involved in the etiology of dental caries, periodontal disease, cystic fibrosis (CF) airway infections, native valve endocarditis, chronic bacterial prostatitis, otitis media, and vaginal infections. Biofilm microorganisms are also involved in implant-related infections, in which adherent microbial populations form on the surfaces of catheters, prosthetic heart valves, joint replacements, and other devices (Donlan R M. Biofilms and device-associated infections. Emerg Infect Dis 2001; 7:277-81).

The bacterium *Salmonella enterica* serovar *typhi* (*S. typhi*) is the causative agent of typhoid fever, infecting and killing an estimated 21 million and 200,000 individuals each year, respectively. *S. typhi* will persist in the gallbladder of 3-5% of individuals, after resolution of the acute infection, through an asymptomatic chronic carrier state, during which fecal shedding allows the bacteria to spread. In this chronic carrier state, *S. typhi* forms biofilms—organized, multicellular communities encapsulated in an extracellular matrix comprised of polysaccharides, proteins, and extracellular DNA—on gallstones. It is believe that the primary reservoir of bacteria in asymptomatic chronic carriers is the gallbladder.

Despite advances in research directed to mitigating the spread of infectious diseases associated with asymptomatic carriers, e.g., biofilms associated with the gallbladder following infection with *Salmonella enterica* serovar *typhi* (*S. typhi*), there is still a scarcity of compounds that are both potent and efficacious for the treatment of biofilms in such clinical situations. These needs and other needs are satisfied by the present disclosure.

SUMMARY

In accordance with the purpose(s) of the disclosure, as embodied and broadly described herein, the disclosure, in one aspect, relates to compositions and methods for dispersing *Salmonella* biofilms. In various aspects, the disclosed compositions can be used in methods of treating a persistent *Salmonella* infection, including an asymptomatic infection. Such infections can colonize a variety of tissues, including the gall-bladder. Also disclosed are methods of treating typhoid fever. Also disclosed are methods for mitigating or preventing secondary outbreaks of typhoid fever by treating asymptomatic subjects who had been symptomatic for typhoid fever at a previous time.

Disclosed are pharmaceutical compositions comprising a therapeutically effective amount of a compound having a structure represented by a formula:

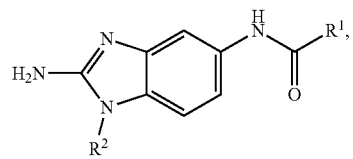

wherein R 1 is selected from a C1-C12 alkyl, a C3-C12 cycloalkyl; and a substituted aryl; and wherein R 2 is selected from a C1-C12 alkyl, a C3-C12 cycloalkyl; and a substituted aryl;

Also disclosed are methods for treatment of a *Salmonella enterica* clinical condition, comprising administering to a subject in need thereof a disclosed pharmaceutical composition.

Also disclosed are methods inhibiting formation of a biofilm in a subject comprising the step of administering to the subject in need thereof a disclosed pharmaceutical composition.

Also disclosed are methods for dispersing a biofilm in a subject comprising the step of administering to the subject in need thereof a disclosed pharmaceutical composition.

Also disclosed are uses of a disclosed pharmaceutical composition.

Also disclosed are uses of a disclosed compound, or a pharmaceutically acceptable salt thereof, in the manufacture of a medicament for the treatment of of *Salmonella enterica* clinical condition in a subject in need thereof.

Also disclosed are methods for the manufacture of a medicament for the treatment of of *Salmonella enterica* clinical condition in a subject in need thereof comprising combining at least one disclosed compound, or a pharmaceutically acceptable salt thereof with a pharmaceutically acceptable carrier or diluent.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE FIGURES

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3A shows the effect of 20 µM of indicated compound (M4-M8) on inhibition of formation of biofilms by S. typhimurium (JSG210) compared to control treatment with 1% DMSO. FIG. 3B shows the effect of 20 µM of indicated compound (M4-M8) on dispersal of biofilms formed by S. typhimurium (JSG210) compared to control treatment with 1% DMSO.

FIG. 4A shows the effect of a representative disclosed compound, compound M4, on inhibition of formation of biofilms by S. typhimurium (JSG210) at the indicated concentrations. The $EC_{50}$ value for inhibition of biofilm formation was calculated from the data to be 8.1 µM. FIG. 3B shows the effect of a representative disclosed compound, compound M4, on inhibition on dispersal of biofilms formed by S. typhimurium (JSG210) at the indicated concentrations. The $EC_{50}$ value for inhibition of biofilm dispersal was calculated from the data to be 20.3 µM.

FIG. 5A shows representative data for a cell death assay using S. typhimurium (JSG210). Briefly, S. typhimurium (JSG210) was grown in the presence of a representative disclosed compound, compound M4, present at a concentration of 10 µM for 24 hours, followed by determination of viability measured by drip plating at T=0, 2, 5, 15, 20, 24 hours. 3 biological replicates were tested. The data show that the compound was not associated with any toxicity. FIG. 5B shows representative data obtained in a toxicity assay using Galleria mellonella larvae. Briefly, a representative disclosed compound, compound M4, was injected into last left proleg of Galleria mellonella larvae at 400 mg/kg and assessed at 24-hour intervals over 5 days. The study was repeated 3 times using 10 larvae per experiment group. The data show no significant toxicity in Galleria mellonella larvae.

Figure 1:
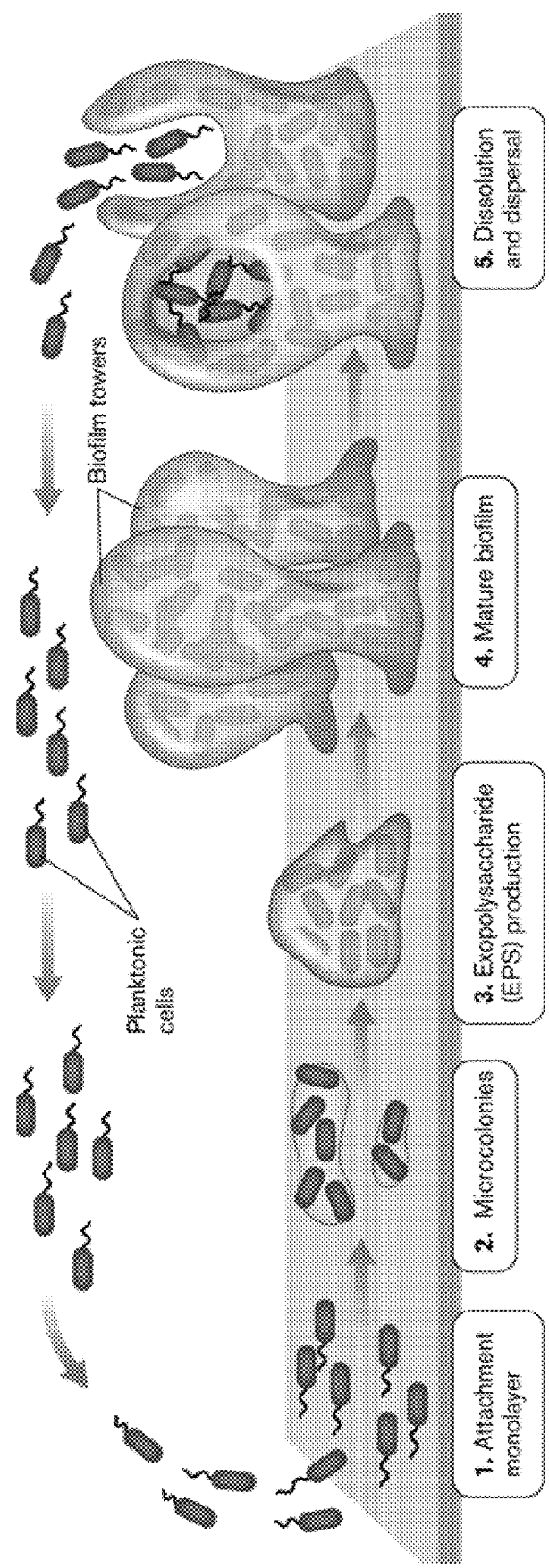
FIG. 1 shows a schematic representation of biofilm formation and dispersal.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

A. Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by," "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a biofilm," "a compound," or "a subject," including, but not limited to, two or more such biofilms, compounds, or subjects.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, $\pi$-$\pi$ interactions, cation-$\pi$ interactions, anion-$\pi$ interactions, polar $\pi$-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as a *Salmonella enterica* infection, *Salmonella* chronic carriage, and/or a biofilm associated with a *Salmo-*

*nella enterica* infection, including an active infection or an asymptomatic infection. The effect can be therapeutic in terms of a partial or complete cure of a disease, condition, symptom or adverse effect attributed to the disease, disorder, or condition. The term "treatment" as used herein can include any treatment of a *Salmonella enterica* infection, *Salmonella* chronic carriage, and/or a biofilm associated with a *Salmonella enterica* infection in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C1-to-C6 alkyl esters and C5-to-C7 cycloalkyl esters, although C1-to-C4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C1-to-C6 alkyl amines and secondary C1-to-C6 dialkyl amines. In the case of secondary amines, the amine can also be in the form of a 5- or 6-membered heterocycle containing one nitrogen atom. Amides derived from ammonia, C1-to-C3 alkyl primary amides and C1-to-C2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added.

The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

It is understood, that unless otherwise specified, temperatures referred to herein are based on atmospheric pressure (i.e. one atmosphere).

Described herein are compounds and pharmaceutical compositions that have therapeutic or clinical utility. Also described herein are methods of administering the disclosed compounds or pharmaceutical compositions to a subject in need thereof. In some aspects, the subject can have a *Salmonella enterica* infection, *Salmonella* chronic carriage, and/or a biofilm associated with a *Salmonella enterica* infection. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

B. Compounds

In various aspects, a disclosed compound has a structure represented by a formula:

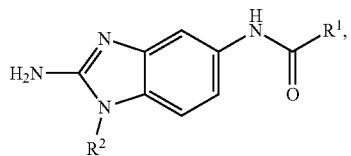

wherein $R^1$ is selected from a C1-C12 alkyl, a C3-C12 cycloalkyl; and a substituted aryl; and wherein $R^2$ is selected from a C1-C12 alkyl, a C3-C12 cycloalkyl; and a substituted aryl; or a pharmaceutically acceptable salt thereof.

In some aspects, $R^1$ is selected from a C1-C12 alkyl and a substituted aryl. Alternatively, $R^1$ can be a C1-C12 alkyl. In a further aspect, $R^1$ is a C1-C6 alkyl. In a still further aspect, $R^1$ is selected from methyl, ethyl, propyl, isopropyl, tent-butyl, sec-butyl, isobutyl, neopentyl, isopentyl, sec-pentyl, tent-pentyl, 3,3-dimethylbutan-2-yl, and 2,3-dimethylbutan-2-yl.

In various aspects, $R^1$ is a substituted aryl. For example, $R^1$ can be a structure represented by a formula:

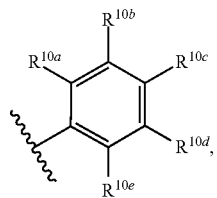

wherein each of $R^{10a}$, $R^{10b}$, $R^{10c}$, $R^{10d}$, and $R^{10e}$ is independently selected from hydrogen, halogen, C1-C6 alkyl, C1-C6 alkoxy, and C1-C6 haloalkyl, provided that at least one of $R^{10a}$, $R^{10b}$, $R^{10c}$, $R^{10d}$, and $R^{10e}$ is not hydrogen. In a further aspect, each of $R^{10a}$, $R^{10b}$, $R^{10c}$, $R^{10d}$, and $R^{10e}$ is independently selected from hydrogen, halogen, C1-C6 alkyl, and C1-C6 alkoxy, provided that two $R^{10a}$, $R^{10b}$, $R^{10c}$, $R^{10d}$, and $R^{10e}$ are hydrogen. In a still further aspect, each of $R^{10a}$, $R^{10b}$, $R^{10c}$, $R^{10d}$, and $R^{10e}$ is independently selected from hydrogen, bromo, chloro, fluoro, C1-C3 alkyl, and C1-C3 alkoxy, provided that at least one of $R^{10a}$, $R^{10b}$, $R^{10c}$, $R^{10d}$, and $R^{10e}$ is not hydrogen. In a yet further aspect, each of $R^{10a}$, $R^{10b}$, $R^{10c}$, $R^{10d}$, and $R^{10e}$ is independently selected from hydrogen, bromo, chloro, C1-C3 alkyl, and C1-C3 alkoxy, provided that at least one of $R^{10a}$, $R^{10b}$, $R^{10c}$, $R^{10d}$, and $R^{10e}$ is not hydrogen. In an even further aspect, each of $R^{10a}$, $R^{10b}$, $R^{10c}$, $R^{10d}$, and $R^{10e}$ is independently selected from hydrogen, bromo, and chloro, provided that at least one of $R^{10a}$, $R^{10b}$, $R^{10c}$, $R^{10d}$, and $R^{10e}$ is not hydrogen. In an yet further aspect, each of $R^{10a}$, $R^{10b}$, $R^{10c}$, $R^{10d}$, and $R^{10e}$ is independently selected from hydrogen, bromo, and chloro, provided that two of $R^{10a}$, $R^{10b}$, $R^{10c}$, $R^{10d}$, and $R^{10e}$ are hydrogen. In a still further aspect, $R^{10a}$, $R^{10b}$, $R^{10c}$, $R^{10d}$, and $R^{10e}$ is independently selected from hydrogen, bromo, and chloro, provided that three of $R^{10a}$, $R^{10b}$, $R^{10c}$, $R^{10d}$, and $R^{10e}$ are hydrogen. In various further aspects, each of $R^{10a}$, $R^{10b}$, $R^{10c}$, $R^{10d}$, and $R^{10e}$ is independently selected from hydrogen, bromo, and chloro, provided that four of $R^{10a}$, $R^{10b}$, $R^{10c}$, $R^{10d}$, and $R^{10e}$ are hydrogen.

In a further aspect, $R^1$ is a structure represented by a formula:

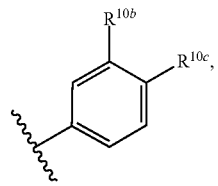

wherein each of $R^{10b}$ and $R^{10c}$ is independently selected from halogen, C1-C6 alkyl, C1-C6 alkoxy, and C1-C6 haloalkyl. In a still further aspect, each of $R^{10b}$ and $R^{10c}$ is independently selected from hydrogen, halogen, C1-C6 alkyl, and C1-C6 alkoxy. In a yet further aspect, each of $R^{10b}$ and $R^{10c}$ is independently selected from hydrogen, bromo, chloro, fluoro, C1-C3 alkyl, and C1-C3 alkoxy. In an even further aspect, each of $R^{10b}$ and $R^{10c}$ is independently selected from hydrogen, bromo, chloro, C1-C3 alkyl, and C1-C3 alkoxy. In a still further aspect, each of $R^{10b}$ and $R^{10c}$ is independently selected from hydrogen, bromo, and chloro.

In a further aspect, $R^1$ is a structure represented by a formula:

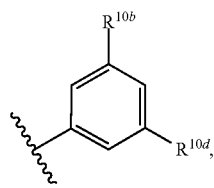

wherein each of $R^{10b}$ and $R^{10d}$ is independently selected from halogen, C1-C6 alkyl, C1-C6 alkoxy, and C1-C6 haloalkyl. In various aspects, each of $R^{10b}$ and $R^{10d}$ is independently selected from hydrogen, halogen, C1-C3 alkyl, and C1-C3 alkoxy. In a further aspect, each of $R^{10b}$ and $R^{10d}$ is independently selected from hydrogen, bromo, chloro, fluoro, C1-C3 alkyl, and C1-C3 alkoxy. In a still further aspect, each of $R^{10b}$ and $R^{10d}$ is independently selected from hydrogen, bromo, chloro, C1-C3 alkyl, and C1-C3 alkoxy. In an even further aspect, each of $R^{10b}$ and $R^{10d}$ is independently selected from hydrogen, bromo, and chloro.

In various aspects, $R^1$ is a structure represented by a formula:

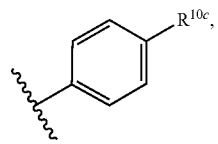

wherein $R^{10c}$ is selected from halogen, C1-C6 alkyl, C1-C6 alkoxy, and C1-C6 haloalkyl. In a further aspect, $R^{10c}$ is selected from hydrogen, halogen, C1-C6 alkyl, and C1-C6 alkoxy. In a still further aspect, $R^{10c}$ is selected from hydrogen, bromo, chloro, fluoro, C1-C3 alkyl, and C1-C3 alkoxy. In a yet further aspect, $R^{10c}$ is selected from hydrogen, bromo, chloro, C1-C3 alkyl, and C1-C3 alkoxy. In an even further aspect, $R^{10c}$ is selected from hydrogen, bromo, and chloro.

In various aspects, a disclosed compound has a structure represented by a formula:

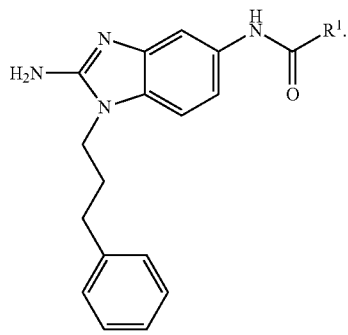

In various aspects, a disclosed compound has a structure represented by a formula:

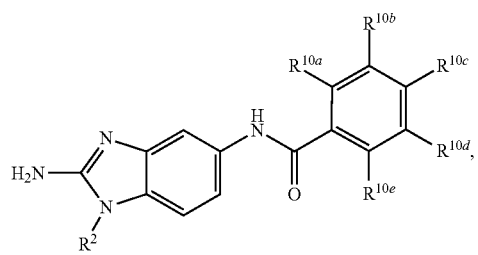

wherein each of $R^{10a}$, $R^{10b}$, $R^{10c}$, $R^{10d}$, and $R^{10e}$ is independently selected from hydrogen, halogen, C1-C6 alkyl, C1-C6 alkoxy, and C1-C6 haloalkyl, provided that at least one of $R^{10a}$, $R^{10b}$, $R^{10c}$, $R^{10d}$, and $R^{10e}$ is not hydrogen. In a further aspect, each of $R^{10a}$, $R^{10b}$, $R^{10c}$, $R^{10d}$, and $R^{10e}$ is independently selected from hydrogen, halogen, C1-C6 alkyl, and C1-C6 alkoxy, provided that two $R^{10a}$, $R^{10b}$, $R^{10c}$, $R^{10d}$, and $R^{10e}$ are hydrogen. In a still further aspect, each of $R^{10a}$, $R^{10b}$, $R^{10c}$, $R^{10d}$, and $R^{10e}$ is independently selected from hydrogen, bromo, chloro, fluoro, C1-C3 alkyl, and C1-C3 alkoxy, provided that at least one of $R^{10a}$, $R^{10b}$, $R^{10c}$, $R^{10d}$, and $R^{10e}$ is not hydrogen. In a yet further aspect, each of $R^{10a}$, $R^{10b}$, $R^{10c}$, $R^{10d}$, and $R^{10e}$ is independently selected from hydrogen, bromo, chloro, C1-C3 alkyl, and C1-C3 alkoxy, provided that at least one of $R^{10a}$, $R^{10b}$, $R^{10c}$, $R^{10d}$, and $R^{10e}$ is not hydrogen. In an even further aspect, each of $R^{10a}$, $R^{10b}$, $R^{10c}$, $R^{10d}$, and $R^{10e}$ is independently selected from hydrogen, bromo, and chloro, provided that at least one of $R^{10a}$, $R^{10b}$, $R^{10c}$, $R^{10d}$, and $R^{10e}$ is not hydrogen. In an yet further aspect, each of $R^{10a}$, $R^{10b}$, $R^{10c}$, $R^{10d}$, and $R^{10e}$ is independently selected from hydrogen, bromo, and chloro, provided that two of $R^{10a}$, $R^{10b}$, $R^{10c}$, $R^{10d}$, and $R^{10e}$ are hydrogen. In a still further aspect, $R^{10a}$, $R^{10b}$, $R^{10c}$, $R^{10d}$, and $R^{10e}$ is independently selected from hydrogen, bromo, and chloro, provided that three of $R^{10a}$, $R^{10b}$, $R^{10c}$, $R^{10d}$, and $R^{10e}$ are hydrogen. In various further aspects, each of $R^{10a}$, $R^{10b}$, $R^{10c}$, $R^{10d}$, and $R^{10e}$ is independently selected from hydrogen, bromo, and chloro, provided that four of $R^{10a}$, $R^{10b}$, $R^{10c}$, $R^{10d}$, and $R^{10e}$ are hydrogen.

In various aspects, a disclosed compound has a structure represented by a formula:

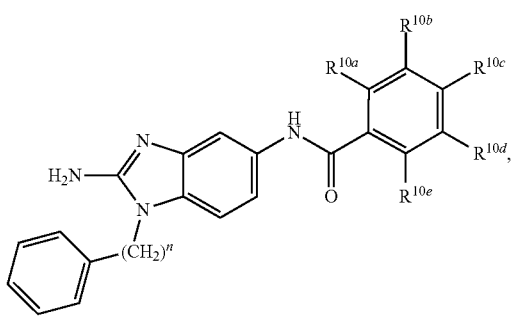

wherein each of $R^{10a}$, $R^{10b}$, $R^{10c}$, $R^{10d}$, and $R^{10e}$ is independently selected from hydrogen, halogen, C1-C6 alkyl, C1-C6 alkoxy, and C1-C6 haloalkyl, provided that at least one of $R^{10a}$, $R^{10b}$, $R^{10c}$, $R^{10d}$, and $R^{10e}$ is not hydrogen. In a further aspect, each of $R^{10a}$, $R^{10b}$, $R^{10c}$, $R^{10d}$, and $R^{10e}$ is independently selected from hydrogen, halogen, C1-C6 alkyl, and C1-C6 alkoxy, provided that two $R^{10a}$, $R^{10b}$, $R^{10c}$, $R^{10d}$, and $R^{10e}$ are hydrogen. In a still further aspect, each of $R^{10a}$, $R^{10b}$, $R^{10c}$, $R^{10d}$, and $R^{10e}$ is independently selected from hydrogen, bromo, chloro, fluoro, C1-C3 alkyl, and C1-C3 alkoxy, provided that at least one of $R^{10a}$, $R^{10b}$, $R^{10c}$, $R^{10d}$, and $R^{10e}$ is not hydrogen. In a yet further aspect, each of $R^{10a}$, $R^{10b}$, $R^{10c}$, $R^{10d}$, and $R^{10e}$ is independently selected from hydrogen, bromo, chloro, C1-C3 alkyl, and C1-C3 alkoxy, provided that at least one of $R^{10a}$, $R^{10b}$, $R^{10c}$, $R^{10d}$, and $R^{10e}$ is not hydrogen. In an even further aspect, each of $R^{10a}$, $R^{10b}$, $R^{10c}$, $R^{10d}$, and $R^{10e}$ is independently selected from hydrogen, bromo, and chloro, provided that at least one of $R^{10a}$, $R^{10b}$, $R^{10c}$, $R^{10d}$, and $R^{10e}$ is not hydrogen. In an yet further aspect, each of $R^{10a}$, $R^{10b}$, $R^{10c}$, $R^{10d}$, and $R^{10e}$ is independently selected from hydrogen, bromo, and chloro, provided that two of $R^{10a}$, $R^{10b}$, $R^{10c}$, $R^{10d}$, and $R^{10e}$ are hydrogen. In a still further aspect, $R^{10a}$, $R^{10b}$, $R^{10c}$, $R^{10d}$, and $R^{10e}$ is independently selected from hydrogen, bromo, and chloro, provided that three of $R^{10a}$, $R^{10b}$, $R^{10c}$, $R^{10d}$, and $R^{10e}$ are hydrogen. In various further aspects, each of $R^{10a}$, $R^{10b}$, $R^{10c}$, $R^{10d}$, and $R^{10e}$ is independently selected from hydrogen, bromo, and chloro, provided that four of $R^{10a}$, $R^{10b}$, $R^{10c}$, $R^{10d}$, and $R^{10e}$ are hydrogen.

In various aspects, a disclosed compound has a structure represented by a formula:

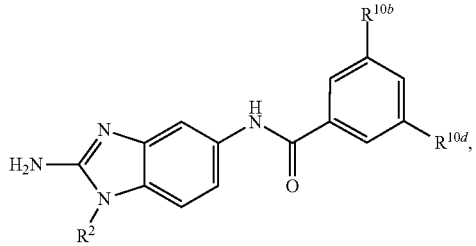

wherein each of $R^{10b}$ and $R^{10d}$ is independently selected from halogen, C1-C6 alkyl, C1-C6 alkoxy, and C1-C6 haloalkyl. In various aspects, each of $R^{10b}$ and $R^{10d}$ is independently selected from hydrogen, halogen, C1-C3 alkyl, and C1-C3 alkoxy. In a further aspect, each of $R^{10b}$ and $R^{10d}$ is independently selected from hydrogen, bromo, chloro, fluoro, C1-C3 alkyl, and C1-C3 alkoxy. In a still further aspect, each of $R^{10b}$ and $R^{10d}$ is independently selected from hydrogen, bromo, chloro, C1-C3 alkyl, and C1-C3 alkoxy. In an even further aspect, each of $R^{10b}$ and $R^{10d}$ is independently selected from hydrogen, bromo, and chloro.

In various aspects, a disclosed compound has a structure represented by a formula:

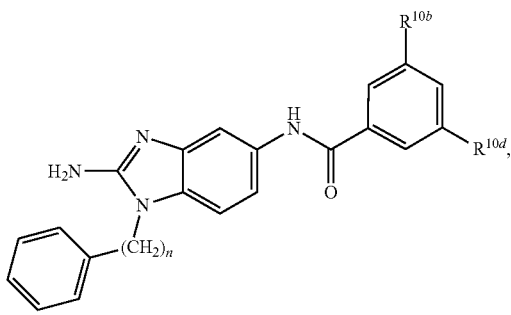

wherein each of $R^{10b}$ and $R^{10d}$ is independently selected from halogen, C1-C6 alkyl, C1-C6 alkoxy, and C1-C6 haloalkyl; and wherein n is an integer selected from 0, 1, 2, 3, 4, 5, 6, 7, 8, 9, 10, 11, and 12. In various aspects, each of $R^{10b}$ and $R^{10d}$ is independently selected from hydrogen, halogen, C1-C3 alkyl, and C1-C3 alkoxy. In a further aspect, each of $R^{10b}$ and $R^{10d}$ is independently selected from hydrogen, bromo, chloro, fluoro, C1-C3 alkyl, and C1-C3 alkoxy. In a still further aspect, each of $R^{10b}$ and $R^{10d}$ is independently selected from hydrogen, bromo, chloro, C1-C3 alkyl, and C1-C3 alkoxy. In an even further aspect, each of $R^{10b}$ and $R^{10d}$ is independently selected from hydrogen, bromo, and chloro.

In various aspects, a disclosed compound has a structure represented by a formula:

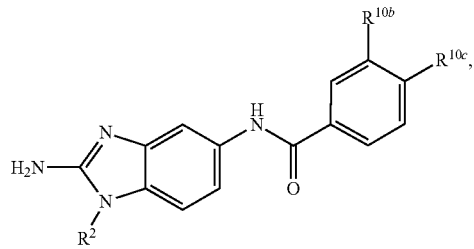

wherein each of $R^{10b}$ and $R^{10c}$ is independently selected from halogen, C1-C6 alkyl, C1-C6 alkoxy, and C1-C6 haloalkyl. In a still further aspect, each of $R^{10b}$ and $R^{10c}$ is independently selected from hydrogen, halogen, C1-C6 alkyl, and C1-C6 alkoxy. In a yet further aspect, each of $R^{10b}$ and $R^{10c}$ is independently selected from hydrogen, bromo, chloro, fluoro, C1-C3 alkyl, and C1-C3 alkoxy. In an even further aspect, each of $R^{10b}$ and $R^{10c}$ is independently selected from hydrogen, bromo, chloro, C1-C3 alkyl, and C1-C3 alkoxy. In a still further aspect, each of $R^{10b}$ and $R^{10c}$ is independently selected from hydrogen, bromo, and chloro.

In various aspects, a disclosed compound has a structure represented by a formula:

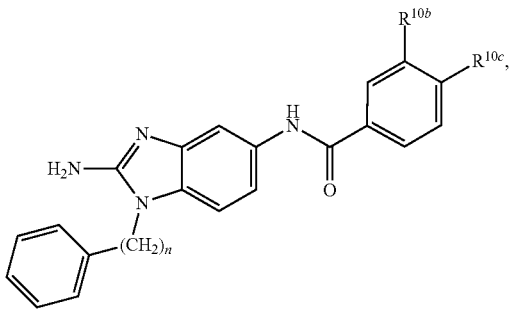

wherein each of $R^{10b}$ and $R^{10c}$ is independently selected from halogen, C1-C6 alkyl, C1-C6 alkoxy, and C1-C6 haloalkyl; and wherein n is an integer selected from 0, 1, 2, 3, 4, 5, 6, 7, 8, 9, 10, 11, and 12. In a still further aspect, each of $R^{10b}$ and $R^{10c}$ is independently selected from hydrogen, halogen, C1-C6 alkyl, and C1-C6 alkoxy. In a yet further aspect, each of $R^{10b}$ and $R^{10c}$ is independently selected from hydrogen, bromo, chloro, fluoro, C1-C3 alkyl, and C1-C3 alkoxy. In an even further aspect, each of $R^{10b}$ and $R^{10c}$ is independently selected from hydrogen, bromo, chloro, C1-C3 alkyl, and C1-C3 alkoxy. In a still further aspect, each of $R^{10b}$ and $R^{10c}$ is independently selected from hydrogen, bromo, and chloro.

In various aspects, a disclosed compound has a structure represented by a formula:

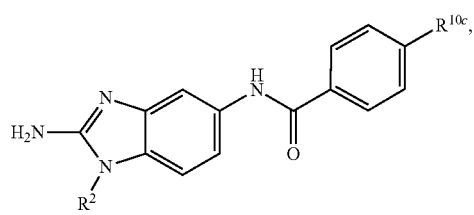

wherein R$^{10c}$ is selected from halogen, C1-C6 alkyl, C1-C6 alkoxy, and C1-C6 haloalkyl. In a further aspect, R$^{10c}$ is selected from hydrogen, halogen, C1-C6 alkyl, and C1-C6 alkoxy. In a still further aspect, R$^{10c}$ is selected from hydrogen, bromo, chloro, fluoro, C1-C3 alkyl, and C1-C3 alkoxy. In a yet further aspect, R$^{10c}$ is selected from hydrogen, bromo, chloro, C1-C3 alkyl, and C1-C3 alkoxy. In an even further aspect, R$^{10c}$ is selected from hydrogen, bromo, and chloro.

In various aspects, a disclosed compound has a structure represented by a formula:

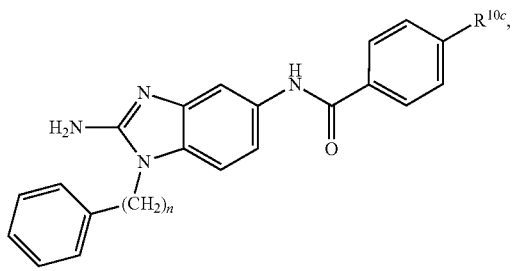

wherein R$^{10c}$ is selected from halogen, C1-C6 alkyl, C1-C6 alkoxy, and C1-C6 haloalkyl; and wherein n is an integer selected from 0,1, 2, 3, 4, 5, 6, 7, 8, 9, 10, 11, and 12. In a further aspect, R$^{10c}$ is selected from hydrogen, halogen, C1-C6 alkyl, and C1-C6 alkoxy. In a still further aspect, R$^{10c}$ is selected from hydrogen, bromo, chloro, fluoro, C1-C3 alkyl, and C1-C3 alkoxy. In a yet further aspect, R$^{10c}$ is selected from hydrogen, bromo, chloro, C1-C3 alkyl, and C1-C3 alkoxy. In an even further aspect, R$^{10c}$ is selected from hydrogen, bromo, and chloro.

In various aspects, a disclosed compound has a structure represented by a formula:

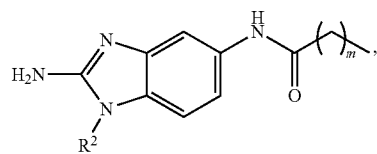

wherein m is an integer selected from 0,1, 2, 3, 4, 5, 6, 7, 8, 9, 10, 11, and 12.

In various aspects, a disclosed compound has a structure represented by a formula:

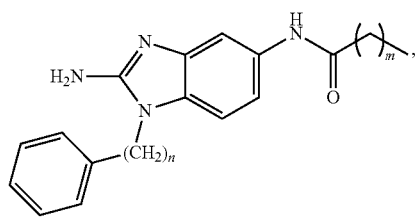

wherein m is an integer selected from 0,1, 2, 3, 4, 5, 6, 7, 8, 9, 10, 11, and 12; and wherein n is an integer selected from 0,1, 2, 3, 4, 5, 6, 7, 8, 9, 10, 11, and 12.

In various aspects, a disclosed compound has a structure represented by a formula:

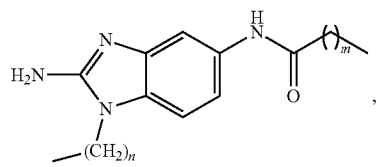

wherein m is an integer selected from 0,1, 2, 3, 4, 5, 6, 7, 8, 9, 10, 11, and 12; and wherein n is an integer selected from 0,1, 2, 3, 4, 5, 6, 7, 8, 9, 10, 11, and 12.

In various aspects, a disclosed compound has a structure represented by a formula:

In various aspects, a disclosed compound has a structure represented by a formula:

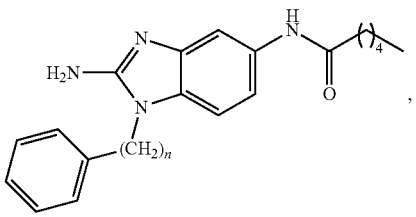

wherein n is an integer selected from 0,1, 2, 3, 4, 5, 6, 7, 8, 9, 10, 11, and 12.

In various aspects, a disclosed compound has a structure represented by a formula:

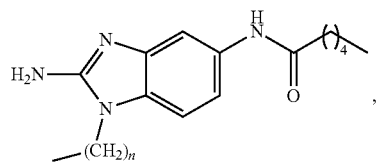

wherein n is an integer selected from 0,1, 2, 3, 4, 5, 6, 7, 8, 9, 10, 11, and 12.

In various aspects, a disclosed compound has a structure represented by a formula:

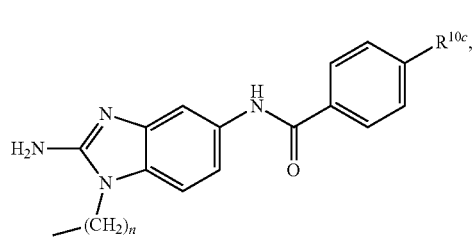

wherein n is an integer selected from 0,1, 2, 3, 4, 5, 6, 7, 8, 9, 10, 11, and 12.

In various aspects, a disclosed compound has a structure represented by a formula:

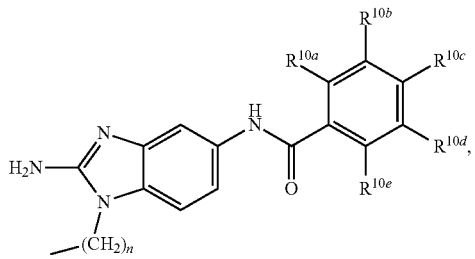

wherein each of $R^{10a}$, $R^{10b}$, $R^{10c}$, $R^{10d}$, and $R^{10e}$ is independently selected from hydrogen, halogen, C1-C6 alkyl, C1-C6 alkoxy, and C1-C6 haloalkyl, provided that at least one of $R^{10a}$, $R^{10b}$, $R^{10c}$, $R^{10d}$, and $R^{10e}$ is not hydrogen. In a further aspect, each of $R^{10a}$, $R^{10b}$, $R^{10c}$, $R^{10d}$, and $R^{10e}$ is independently selected from hydrogen, halogen, C1-C6 alkyl, and C1-C6 alkoxy, provided that two $R^{10a}$, $R^{10b}$, $R^{10c}$, $R^{10d}$, and $R^{10e}$ are hydrogen. In a still further aspect, each of $R^{10a}$, $R^{10b}$, $R^{10c}$, $R^{10d}$, and $R^{10e}$ is independently selected from hydrogen, bromo, chloro, fluoro, C1-C3 alkyl, and C1-C3 alkoxy, provided that at least one of $R^{10a}$, $R^{10b}$, $R^{10c}$, $R^{10d}$, and $R^{10e}$ is not hydrogen. In a yet further aspect, each of $R^{10a}$, $R^{10b}$, $R^{10c}$, $R^{10d}$, and $R^{10e}$ is independently selected from hydrogen, bromo, chloro, C1-C3 alkyl, and C1-C3 alkoxy, provided that at least one of $R^{10a}$, $R^{10b}$, $R^{10c}$, $R^{10d}$, and $R^{10e}$ is not hydrogen. In an even further aspect, each of $R^{10a}$, $R^{10b}$, $R^{10c}$, $R^{10d}$, and $R^{10e}$ is independently selected from hydrogen, bromo, and chloro, provided that at least one of $R^{10a}$, $R^{10b}$, $R^{10c}$, $R^{10d}$, and $R^{10e}$ is not hydrogen. In an yet further aspect, each of $R^{10a}$, $R^{10b}$, $R^{10c}$, $R^{10d}$, and $R^{10e}$ is independently selected from hydrogen, bromo, and chloro, provided that two of $R^{10a}$, $R^{10b}$, $R^{10c}$, $R^{10d}$, and $R^{10e}$ are hydrogen. In a still further aspect, $R^{10a}$, $R^{10b}$, $R^{10c}$, $R^{10d}$, and $R^{10e}$ is independently selected from hydrogen, bromo, and chloro, provided that three of $R^{10a}$, $R^{10b}$, $R^{10c}$, $R^{10d}$, and $R^{10e}$ are hydrogen. In various further aspects, each of $R_{10a}$, $R^{10b}$, $R^{10c}$, $R^{10d}$, and $R^{10e}$ is independently selected from hydrogen, bromo, and chloro, provided that four of $R^{10a}$, $R^{10b}$, $R^{10c}$, $R^{10d}$, and $R^{10e}$ are hydrogen.

In various aspects, a disclosed compound has a structure represented by a formula:

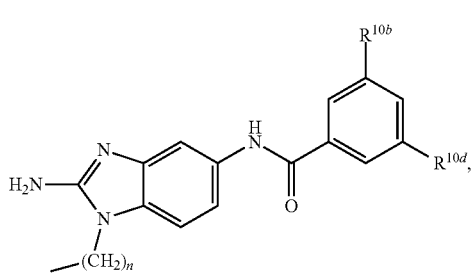

wherein each of $R^{10b}$ and $R^{10d}$ is independently selected from halogen, C1-C6 alkyl, C1-C6 alkoxy, and C1-C6 haloalkyl; and wherein n is an integer selected from 0, 1, 2, 3, 4, 5, 6, 7, 8, 9, 10, 11, and 12. In various aspects, each of $R^{10b}$ and $R^{10d}$ is independently selected from hydrogen, halogen, C1-C3 alkyl, and C1-C3 alkoxy. In a further aspect, each of $R^{10b}$ and $R^{10d}$ is independently selected from hydrogen, bromo, chloro, fluoro, C1-C3 alkyl, and C1-C3 alkoxy. In a still further aspect, each of $R^{10b}$ and $R^{10d}$ is independently selected from hydrogen, bromo, chloro, C1-C3 alkyl, and C1-C3 alkoxy. In an even further aspect, each of $R^{10b}$ and $R^{10d}$ is independently selected from hydrogen, bromo, and chloro.

In various aspects, a disclosed compound has a structure represented by a formula:

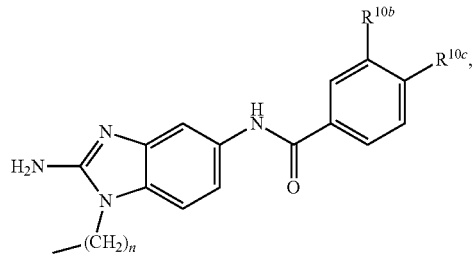

wherein each of $R^{10b}$ and $R^{10c}$ is independently selected from halogen, C1-C6 alkyl, C1-C6 alkoxy, and C1-C6 haloalkyl; and wherein n is an integer selected from 0, 1, 2, 3, 4, 5, 6, 7, 8, 9, 10, 11, and 12. In a still further aspect, each of $R^{10b}$ and $R^{10c}$ is independently selected from hydrogen, halogen, C1-C6 alkyl, and C1-C6 alkoxy. In a yet further aspect, each of $R^{10b}$ and $R^{10c}$ is independently selected from hydrogen, bromo, chloro, fluoro, C1-C3 alkyl, and C1-C3 alkoxy. In an even further aspect, each of $R^{10b}$ and $R^{10c}$ is independently selected from hydrogen, bromo, chloro, C1-C3 alkyl, and C1-C3 alkoxy. In a still further aspect, each of $R^{10b}$ and $R^{10c}$ is independently selected from hydrogen, bromo, and chloro.

In various aspects, a disclosed compound has a structure represented by a formula:

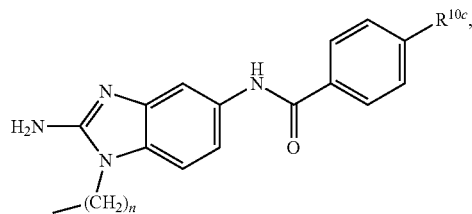

wherein $R^{10c}$ is selected from halogen, C1-C6 alkyl, C1-C6 alkoxy, and C1-C6 haloalkyl; and wherein n is an integer selected from 0, 1, 2, 3, 4, 5, 6, 7, 8, 9, 10, 11, and 12. In a further aspect, $R^{10c}$ is selected from hydrogen, halogen, C1-C6 alkyl, and C1-C6 alkoxy. In a still further aspect, $R^{10c}$ is selected from hydrogen, bromo, chloro, fluoro, C1-C3 alkyl, and C1-C3 alkoxy. In a yet further aspect, $R^{10c}$ is selected from hydrogen, bromo, chloro, C1-C3 alkyl, and C1-C3 alkoxy. In an even further aspect, $R^{10c}$ is selected from hydrogen, bromo, and chloro.

In various aspects, a disclosed compound can be present as:

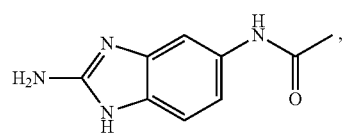

-continued

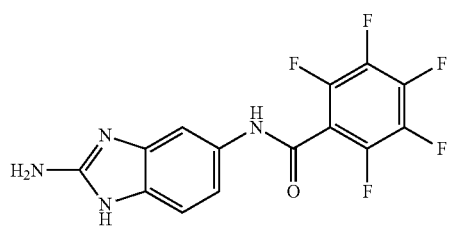

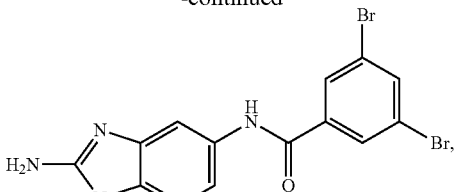

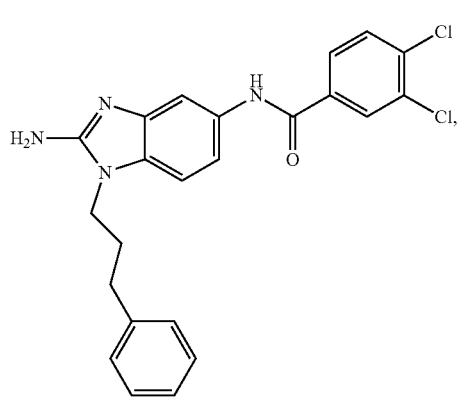

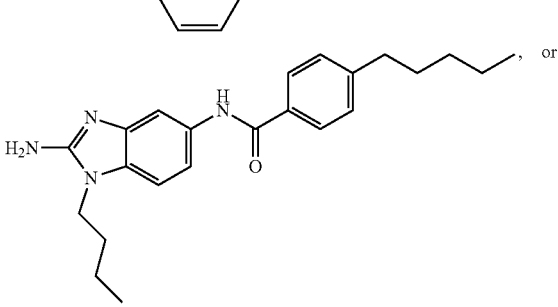

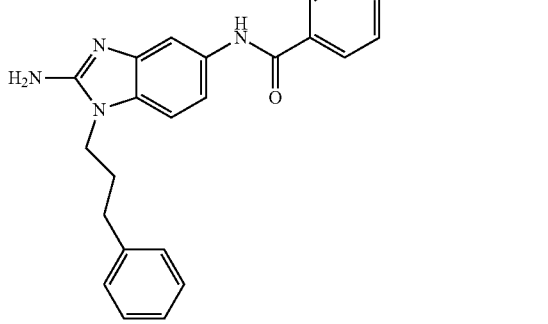

or a subgroup thereof.

In various aspects, it is contemplated herein that the disclosed compounds further comprise their biosteric equivalents. The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity;* in Medicinal Chemistry Third ed., Burger A, ed.; Wiley-Interscience; New York, 1970, 64-80; (ii) Burger, A.; "Isosterism and bioisosterism in drug design"; *Prog. Drug Res.* 1991, 37, 287-371; (iii) Burger A, "Isosterism and bioanalogy in drug design", *Med. Chem. Res.* 1994, 4, 89-92; (iv) Clark R D, Ferguson A M, Cramer R D, "Bioisosterism and molecular diversity", *Perspect. Drug Discovery Des.* 1998, 9/10/11, 213-224; (v) Koyanagi T, Haga T, "Bioisosterism in agro-chemicals", *ACS Symp. Ser.* 1995, 584, 15-24; (vi) Kubinyi H, "Molecular similarities. Part 1. Chemical structure and biological activity", *Pharm. Unserer Zeit* 1998, 27, 92-106; (vii) Lipinski C A.; "Bioisosterism in drug design"; *Annu.*

Rep. Med. Chem. 1986, 21, 283-91; (viii) Patani G A, LaVoie E J, "Bioisosterism: A rational approach in drug design", *Chem. Rev.* (Washington, D.C.) 1996, 96, 3147-3176; (ix) Soskic V, Joksimovic J, "Bioisosteric approach in the design of new dopaminergic/serotonergic ligands", *Curr. Med. Chem.* 1998, 5, 493-512 (x) Thornber C W, "Isosterism and molecular modification in drug design", *Chem. Soc. Rev.* 1979, 8, 563-80.

In further aspects, bioisosteres are atoms, ions, or molecules in which the peripheral layers of electrons can be considered substantially identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density. Preferred bioisosteres of esters, amides or carboxylic acids are compounds containing two sites for hydrogen bond acceptance. In one embodiment, the ester, amide or carboxylic acid bioisostere is a 5-membered monocyclic heteroaryl ring, such as an optionally substituted 1H-imidazolyl, an optionally substituted oxazolyl, 1H-tetrazolyl, [1,2,4]triazolyl, or an optionally substituted [1,2,4]oxadiazolyl.

In various aspects, it is contemplated herein that the disclosed compounds further comprise their isotopically-labelled or isotopically-substituted variants, i.e., compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{35}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

In various aspects, the disclosed compounds can possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. In some aspects, provided this is possible, the disclosed compounds can be present in the form of the tautomers.

Thus, methods which are known per se can be used, for example, to separate the disclosed compounds which possess one or more chiral centers and occur as racemates into their optical isomers, i.e., enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

In various aspects, the disclosed compounds can be in the form of a co-crystal. The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Preferred co-crystals include p-toluenesulfonic acid and benzenesulfonic acid.

The term "pharmaceutically acceptable co-crystal" means one that is compatible with the other ingredients of the formulation and not deleterious to the recipient thereof.

In a further aspect, the disclosed compounds can be isolated as solvates and, in particular, as hydrates of a disclosed compound, which can be obtained, for example, by crystallization from a solvent or from aqueous solution. In this connection, one, two, three or any arbitrary number of solvate or water molecules can combine with the compounds according to the invention to form solvates and hydrates.

The disclosed compounds can be used in the form of salts derived from inorganic or organic acids. Pharmaceutically acceptable salts include salts of acidic or basic groups present in the disclosed compounds. Suitable pharmaceutically acceptable salts include base addition salts, including alkali metal salts, e.g., sodium or potassium salts; alkaline earth metal salts, e.g., calcium or magnesium salts; and salts formed with suitable organic ligands, e.g., quaternary ammonium salts, which may be similarly prepared by reacting the drug compound with a suitable pharmaceutically acceptable base. The salts can be prepared in situ during the final isolation and purification of the compounds of the present disclosure; or following final isolation by reacting a free base function, such as a secondary or tertiary amine, of a disclosed compound with a suitable inorganic or organic acid; or reacting a free acid function, such as a carboxylic acid, of a disclosed compound with a suitable inorganic or organic base.

Acidic addition salts can be prepared in situ during the final isolation and purification of a disclosed compound, or separately by reacting moieties comprising one or more nitrogen groups with a suitable acid. In various aspects, acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. In a further aspect, salts further include, but are not limited, to the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, butyrate, camphorate, camphorsulfonate, digluconate, glycerophosphate, hemisulfate, heptanoate, hexanoate, fumarate, hydrochloride, 2-hydroxyethanesulfonate (isethionate), nicotinate, 2-naphthalenesulfonate, oxalate, pectinate, persulfate, 3-phenylpropionate, picrate, pivalate, propionate, succinate, tartrate, thiocyanate, phosphate, glutamate, bicarbonate, undecanoate, and pamoate (i.e., 1,1'-methylene-bis-(2-hydroxy-3-naphthoate)) salts. Also, basic nitrogen-containing groups can be quatemized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

Basic addition salts can be prepared in situ during the final isolation and purification of a disclosed compound, or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like. In further aspects, bases which may be used in the preparation of pharmaceutically acceptable salts include the following: ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

C. Pharmaceutical Compositions

In various aspects, the present disclosure relates to pharmaceutical compositions comprising a therapeutically effective amount of a disclosed compound, or a pharmaceutically acceptable salt thereof, and a pharmaceutically acceptable carrier. In a further aspect, the present disclosure relates to pharmaceutical compositions comprising a therapeutically effective amount of at least one disclosed compound or at least one disclosed product of a method of making a compound, as well as pharmaceutically acceptable salt, hydrate, solvate, or polymorph forms of the disclosed compound or the disclosed product of a method of making compound.

As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed compound, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with a basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example Eudragit® RS), copolymerizates of acrylic and methacrylic acid esters and trimethyl ammonium methacrylate (for example Eudragit® RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik and angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ $\alpha$-, $\beta$- or $\gamma$-cyclodextrins or their derivatives, in particular hydroxyalkyl substituted cyclodextrins, e.g. 2-hydroxypropyl-$\beta$-cyclodextrin or sulfobutyl-$\beta$-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present disclosure may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present disclosure include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present disclosure therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present disclosure include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the disclosure formulated in a pharmaceutically acceptable carrier may also be prepared, placed in an appropriate container, and labeled for treatment of an indicated condition.

Another patch system configuration which can be used by the present disclosure is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present disclosure is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require of inhibiting protein synthesis in a bacterial cell an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for inhibiting protein synthesis in a bacterial cell (e.g., treatment of one or more infectious diseases associated with a bacterial infection) in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed compound, a product of a disclosed method of making, a pharmaceutically acceptable salt, a hydrate thereof, a solvate thereof, a polymorph thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed compound, a product of a disclosed method of making, a pharmaceutically acceptable salt, a hydrate thereof, a solvate thereof, a polymorph thereof, and an anti-microbial agent. The present disclosure also relates to such a combination for use as a medicine. The present disclosure also relates to a product comprising (a) disclosed compound, a product of a disclosed method of making, a pharmaceutically acceptable salt, a hydrate thereof, a solvate thereof, a polymorph thereof, and (b) an additional therapeutic agent that has anti-microbial activity, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

D. Methods of Treating a Clinical Condition Associated with a *Salmonella enterica* Infection In various aspects, the present disclosure provides methods of treating an a *Salmonella enterica* clinical condition comprising administration of a therapeutically effective amount of a disclosed compound, a product of a disclosed method of making a compound, or a disclosed pharmaceutical composition to a subject in need thereof. It is understood that reference to a disclosed compound is inclusive of the disclosed compound, as well as pharmaceutically acceptable salt, hydrate, solvate, or polymorph forms thereof; reference to a product of a disclosed method of making a compound is inclusive of the disclosed product, as well as pharmaceutically acceptable salt, hydrate, solvate, or polymorph forms thereof; and reference to a disclosed pharmaceutical composition is inclusive of a pharmaceutical composition comprising a disclosed compound or a disclosed product of a method of making a compound, as well as pharmaceutically acceptable salt, hydrate, solvate, or polymorph forms of a disclosed compound or a disclosed product of a method of making compound. It is understood that treating a *Salmonella enterica* clinical condition is inclusive of treating, preventing, ameliorating, controlling or reducing the risk of a *Salmonella enterica* clinical condition.

Also provided is a method for the treatment of one or more *Salmonella enterica* clinical conditions in a subject comprising the step of administering to the subject at least one disclosed compound; at least one disclosed pharmaceutical composition; and/or at least one disclosed product in a dosage and amount effective to treat the disorder in the subject. In some aspects, the subject is a human subject.

In a further aspect, the disclosure relates to a method for the treatment of a *Salmonella enterica* clinical condition in a human subject, further comprising the step of identifying a human subject in need of treatment of the infectious diesease.

In a further aspect, the disclosure relates to a method for the treatment of a *Salmonella enterica* clinical condition in a human subject comprising the step of administering to the human subject a therapeutically effective amount of at least one disclosed compound; or a pharmaceutically acceptable salt, hydrate, solvate, or polymorph thereof; wherein the compound is formulated as a lotion, a cream, an ointment, a spray, or a soap.

In a further aspect, the compound is formulated as a solid dosage form. In a still further aspect, the solid dosage form is selected from a capsule, a tablet, a pill, a powder, a granule, an effervescing granule, a gel, a paste, a troche, and a pastille. In yet a further aspect, the solid dosage form is formulated for oral administration.

In a further aspect, the compound is formulated as a liquid dosage form. In a still further aspect, the liquid dosage form is selected from an emulsion, a solution, a suspension, a syrup, and an elixir. In yet a further aspect, the liquid dosage form is formulated for intravenous administration or parenteral administration.

In a further aspect, the disclosure relates to a method for the treatment of a *Salmonella enterica* clinical condition in subject, further comprising administering to the vertebrate animal a therapeutically effective amount of second active agent. In a still further aspect, the second active agent is an antibacterial agent. In yet a further aspect, the antibacterial agent is pencillin, a cephalosporin, a sulfonamide, a tetracycline, a lincosamide, an aminoglycoside, or a fluoroquinolone, or combinations thereof. In an even further aspect, the antibacterial agent comprises a compound selected from amoxicillin, ampicillin, azithromycin, aztreonam, azlocillin, bacitracin, carbenicillin, cefaclor, cefadroxil, cefamandole, cefazolin, cephalexin, cefdinir, cefditoren, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, cycloserin, dalbavancin, dalfopristin, demeclocycline, dicloxacillin, dirithromycin, doxycycline, erythromycin, enrofloxacin, enoxacin, enviomycin, ertepenem, ethambutol, ethionmide, flucloxacillin, fosfomycin, furazolidone, gatifloxacin, gentamicin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, pyrazinamide, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, thioacetazone, thioridazine, ticarcillin, tinidazole, tobramycin, torezolid, tosufloxacin, trimethoprim, troleandomycin, trovafloxacin, and vancomycin, or combinations thereof.

In a further aspect, the second agent comprises a compound selected from amikacin, amoxicillin-clavulanic acid, bedaquiline, capreomycin, ciprofloxacin, clarithromycin, clofazimine, cycloserine, ethambutol, ethionamide, gatifloxacin, imipenem, isoniazid, kanamycin, levofloxacin, meropenem, moxifloxacin, ofloxacin, OPC-7683, para-aminosalicylic acid, pretomanid, pyrazinamide, rifampin, rifapentine, rifabutin, SQ109, streptomycin, sudoterb, terizidone, thiacetazone, viomycin, and combinations thereof. In a yet further aspect, the anti-tuberculosis agent is an aminoglycoside antibiotic, such as kanamycin A, amikacin, tobramycin, dibekacin, gentamicin, sisomicin, netilmicin, neomycin B, neomycin C, paromomycin and streptomycin. In an even further aspect, the anti-tuberculosis agent is a fluroquinolone, such as moxifloxacin, levofloxacin, sparfloxacin, nalidixic acid, ciprofloxacin, cinoxacin, oxolinic acid, piromidic acid, pipemidic acid, rosoxacin, enoxacin, fleroxacin, lomefloxacin, nadifloxacin, norfloxacin, ofloxacin, perfloxacin, rufloxacin, balofloxacin, grepafloxacin, pazufloxacin, temafloxacin, tosufloxacin, clinafloxacin, gatlifloxacin, sitafloxacin, prulifloxacin, delafloxacin, JNJ-Q2, nemofloxacin, danofloxacin, difloxacin, enrofloxacin, ibafloxacin, marbofloxacin, orbifloxacin, sarafloxacin and trovafloxacin. In a still further aspect, the anti-tuberculosis agent is a nitroimidazole antibiotic, such as metronidazole, tinidazole, nimorazole, or combinations thereof.

In a further aspect, the second agent comprises a compound selected from

The compounds are further useful in a method for the prevention, treatment, control, amelioration, or reduction of risk of the *Salmonella enterica* clinical conditions noted herein. The compounds are further useful in a method for the prevention, treatment, control, amelioration, or reduction of risk of the aforementioned *Salmonella enterica* clinical conditions in combination with other agents.

In one aspect, the disclosed compounds can be used in combination with one or more other drugs in the treatment, prevention, control, amelioration, or reduction of risk of *Salmonella enterica* clinical conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present disclosure.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the *Salmonella enterica* clinical conditions for which disclosed compounds are useful. Such other drugs can be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present disclosure.

The weight ratio of a disclosed compound to the second active ingredient can be varied and will depend upon the effective dose of each ingredient. Generally, an effective dose of each will be used. Thus, for example, when a compound of the present disclosure is combined with another agent, the weight ratio of a disclosed compound to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with antibacterial or antimicrobial agents, and combinations thereof, and the like, or the subject compound can be administered in conjunction with the use of physical methods such as with debridement of a wound or infected tissue.

In the treatment of a *Salmonella enterica* clinical condition, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In a further aspect, the present disclosure provides methods of treating a *Salmonella enterica* clinical condition in a subject comprising administering a disclosed compound or a disclosed pharmaceutical composition, and further comprising administering to the subject a therapeutically effective amount of an immunomodulatory agent. In a still further aspect, the immunomodulatory agent is a cytokine, an interleukin, a chemokine, or combinations thereof. In a yet further aspect, the immunomodulatory agent is selected from IL-2, IL-7 and IL-12, IFN-α, IFN-β, IFN-ε, IFN-κ, IFN-ω, IFN-γ, IFN-γ 1b, CCL3, CCL26, CXCL7, and combinations thereof.

In a further aspect, the administering is co-administering of the disclosed compound and the antibacterial agent. In a still further aspect, the co-administration is administration in a substantially simultaneous manner of the disclosed compound and the antibacterial agent. In yet a further aspect, the co-administration is administration in a substantially sequential manner of the disclosed compound and the antibacterial agent.

In a further aspect, the administration in a substantially simultaneous manner comprises a single dose form containing a fixed ratio of the compound and the antibacterial agent. In a still further aspect, the single dose form is a capsule or a tablet. In yet a further aspect, the single dose form is an ampule for a single intravenous administration.

E. Kits

In a further aspect, the present disclosure relates to kits comprising at least one disclosed compound, or a pharmaceutically acceptable salt, hydrate, solvate, or polymorph thereof; a disclosed pharmaceutical composition; and one or more of: (a) at least one agent known to treat an infectious disease; (b) instructions for treating an infectious disease; or (c) instructions for treating a biofilm.

The disclosed compounds and/or pharmaceutical compositions comprising the disclosed compounds can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present invention also features such kits further containing instructions for use.

In a further aspect, the present disclosure also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

As illustrated in FIG. 1, a biofilm is a community of bacteria encased in a self-produced exopolysaccharide (EPS) matrix and adhered to an inert or living surface. The biofilm EPS matrix serves to protect the bacteria from antibiotics, host immune responses, and other environmental threats.

Figure 2:
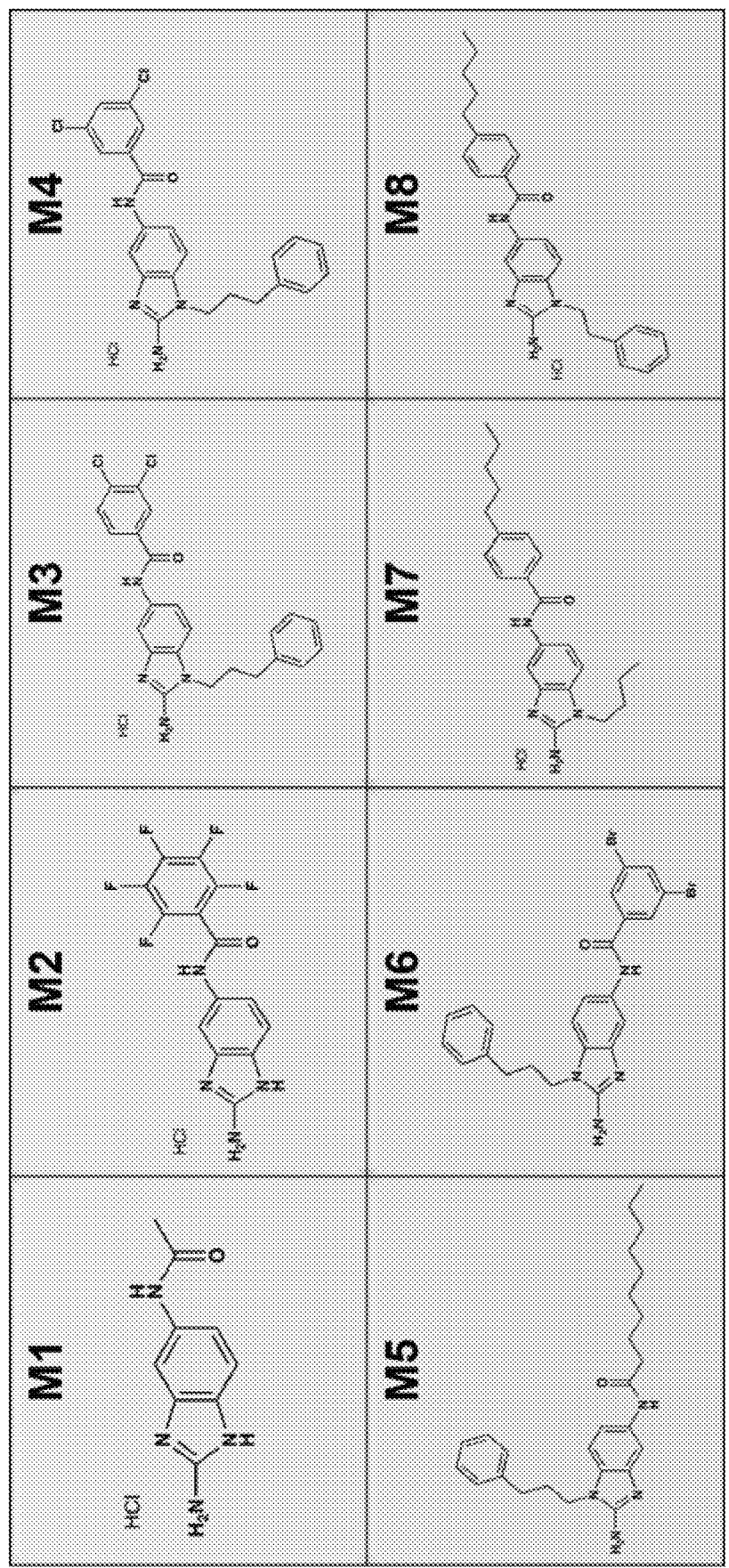
FIG. 2 shows molecular structures for representative disclosed compounds.

Data obtained in assays of representative disclosed compounds M1-M4 showed inhibition of the formation of *S. typhimurium* (JSG210) biofilms. Assays for inhibition of formation of *S. typhimurium* (JSG210) biofilms were also carried out using representative disclosed compounds M4-M8. *S. typhimurium* (JSG210) biofilms are commonly used to study biofilms associated with *S. typhimurium* biofilms. Briefly, the assays utilized were 96-well microtiter plate biofilm assays (Rapid Attachment Assays) were used to compare inhibition of biofilm formation and existing 24-hour biofilm dispersal in the presence of the anti-biofilm compounds M4-M8. *S. typhimurium* (JSG210) was grown overnight in TSB and normalized to OD600 0.8. The structures for the compounds designated M1-M8 are given in FIG. 2.

Figure 3A:
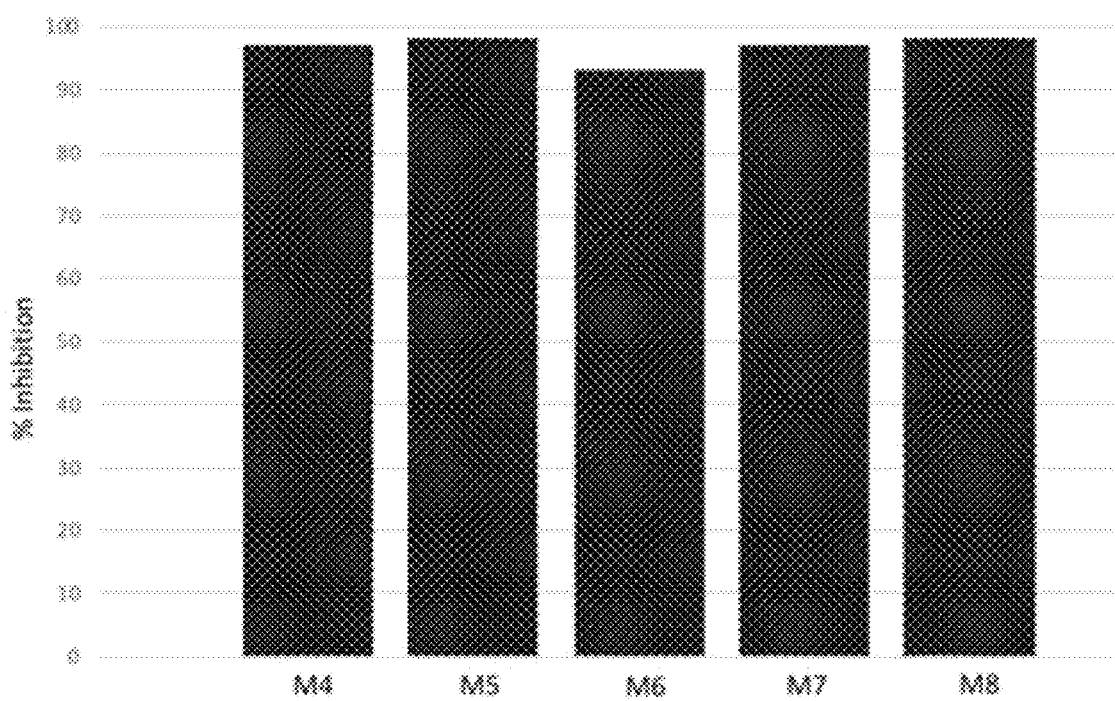
FIGS. 3A-3B show representative data obtained from assays of S. typhimurium biofilm formation and dispersal.
Figure 3B:
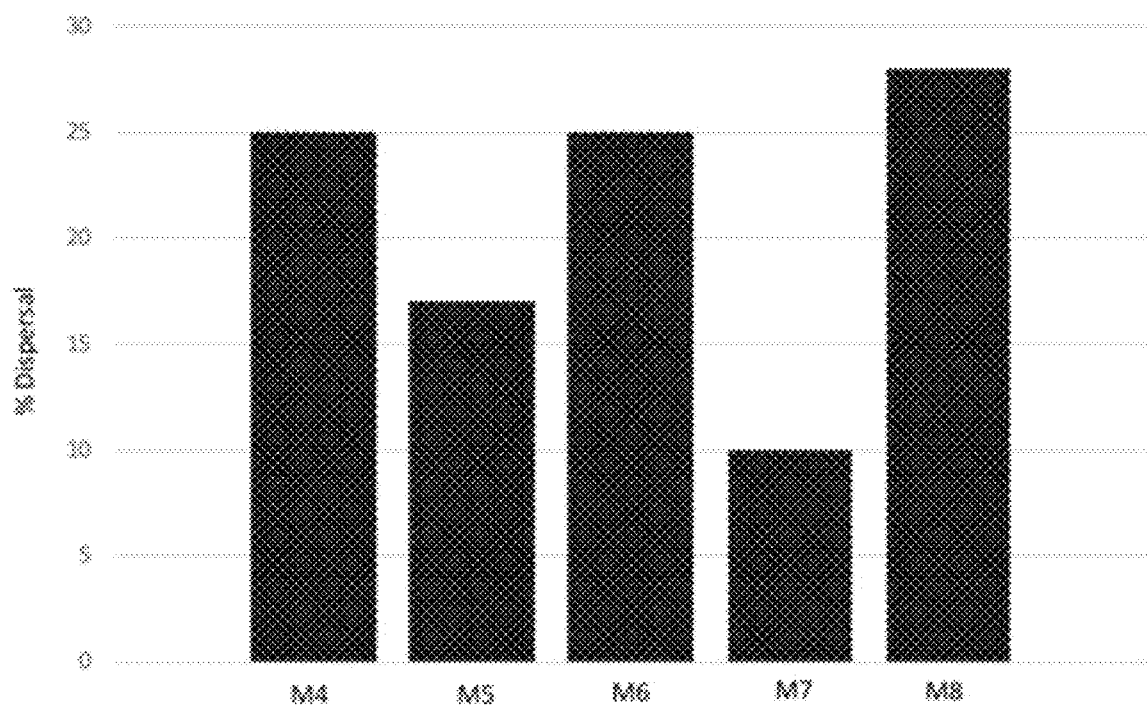

FIGS. 3A and 3B show results of an inhibition assay (FIG. 3A) and dispersal assay (FIG. 3B). JSG210+20 µM compound was plated and grown for 24 hours at 30° C. nutating for the inhibition assay. For the dispersal assay, JSG210 was grown for 24 hours at 30° C. nutating, and the media was replaced on Day 2 and 20 µM compound was added. After 24 hours of growth in the presence of the compound, the 96-well plates were heat fixed and stained with Crystal Violet, and biofilm formation quantified using a microplate reader at 570 nm. Based on results and projected pharmacodynamic properties of representative disclosed compound, compound M4, was investigated in greater detail as a biofilm inhibitor and dispersal agent.

Figure 4B:
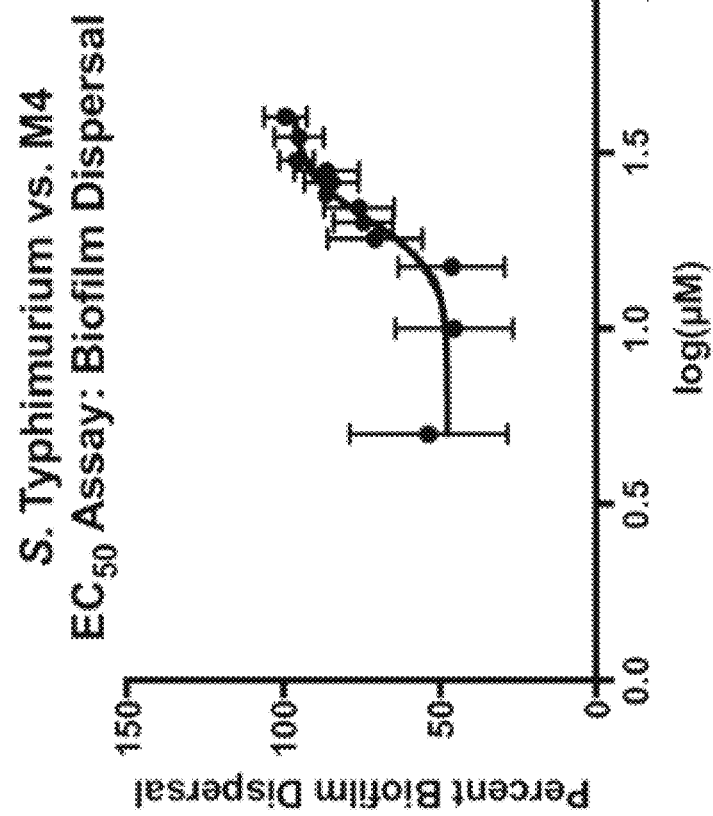
FIGS. 4A-4B show representative data obtained from assays of S. typhimurium biofilm formation and dispersal versus concentration of a representative disclosed compound.
Figure 4A:
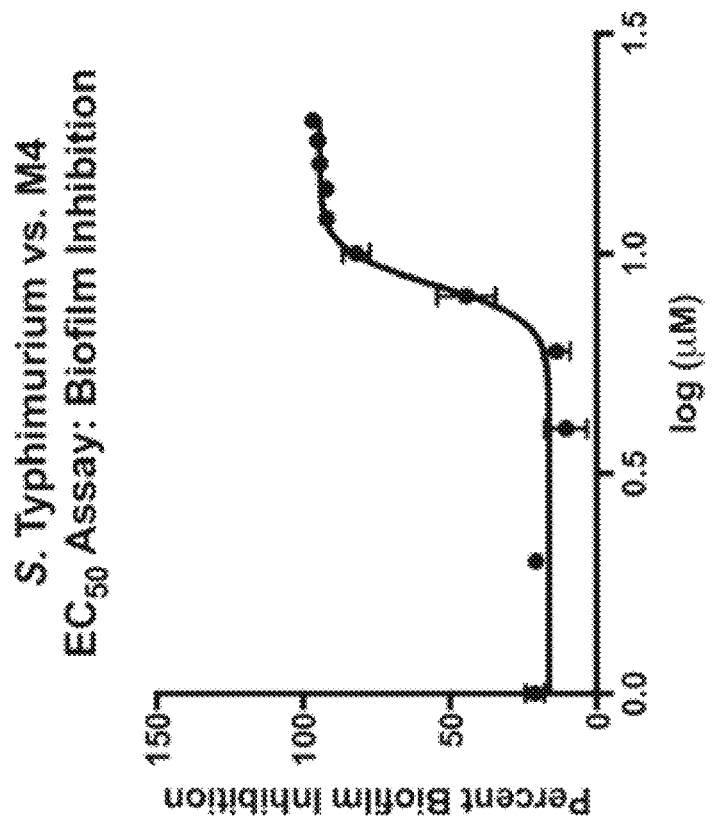

*S. typhimurium* was used to determine $EC_{50}$ values for inhibition of the formation of biofilms and dispersion of existing biofilms by representative disclosed compound, compound M4. The assays were was performed with Rapid Attachment Assay protocol. JSG210 was grown overnight in TSB and grown in 96-well microtiter plate at desired concentration with M4 for 24 hours at 30° C. nutating. For dispersal assay, media was replaced at 24 hours and compound M4 added. After 24 hours of growth in the presence of the compound, the 96-well plates were heat fixed and stained with Crystal Violet, and biofilm formation quantified using a microplate reader at 570 nm. Results are shown in FIGS. 4A and 4B.

Figure 5A:
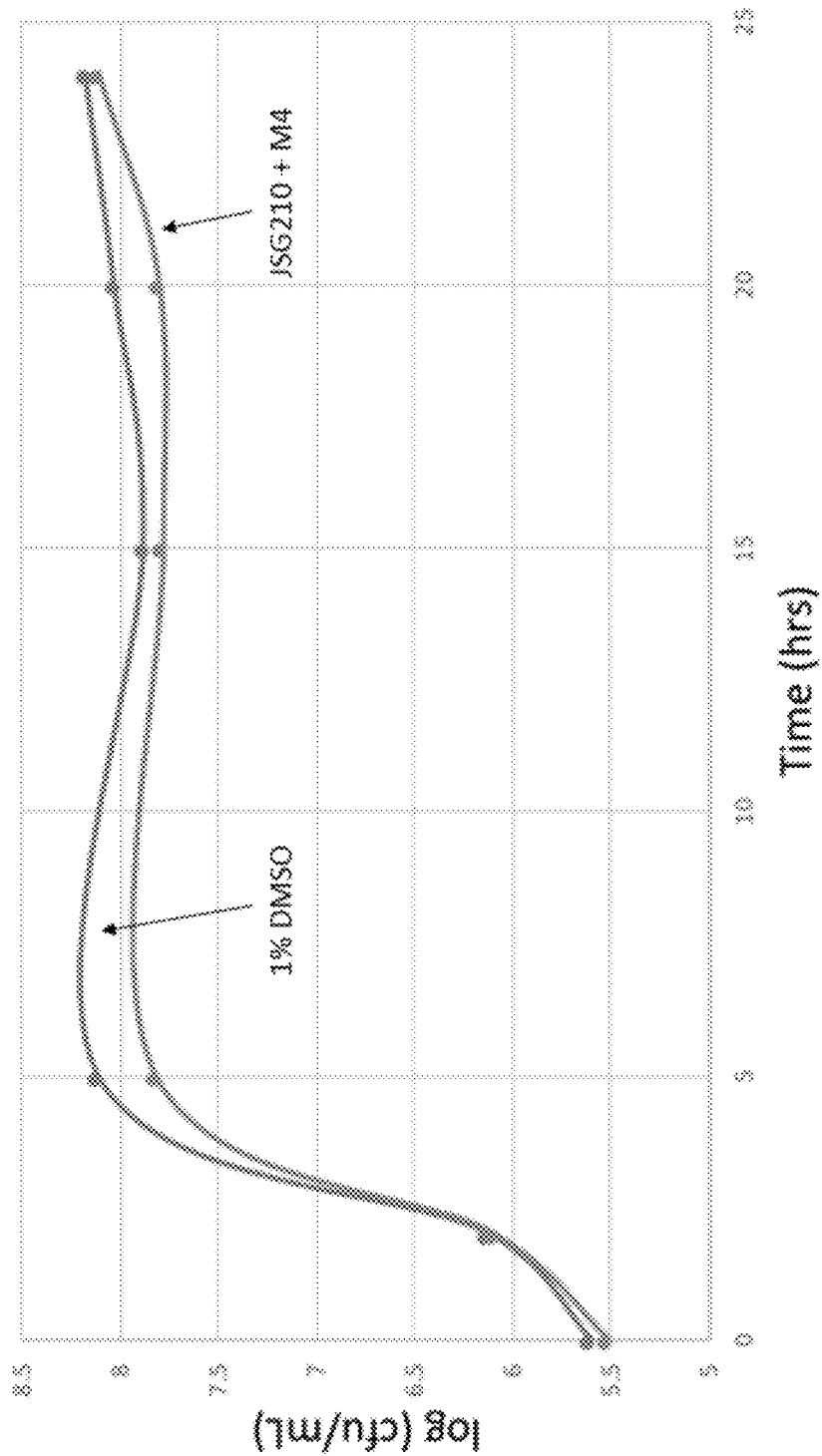
FIGS. 5A-5B show representative toxicity data obtained for a representative disclosed compound.
Figure 5B:
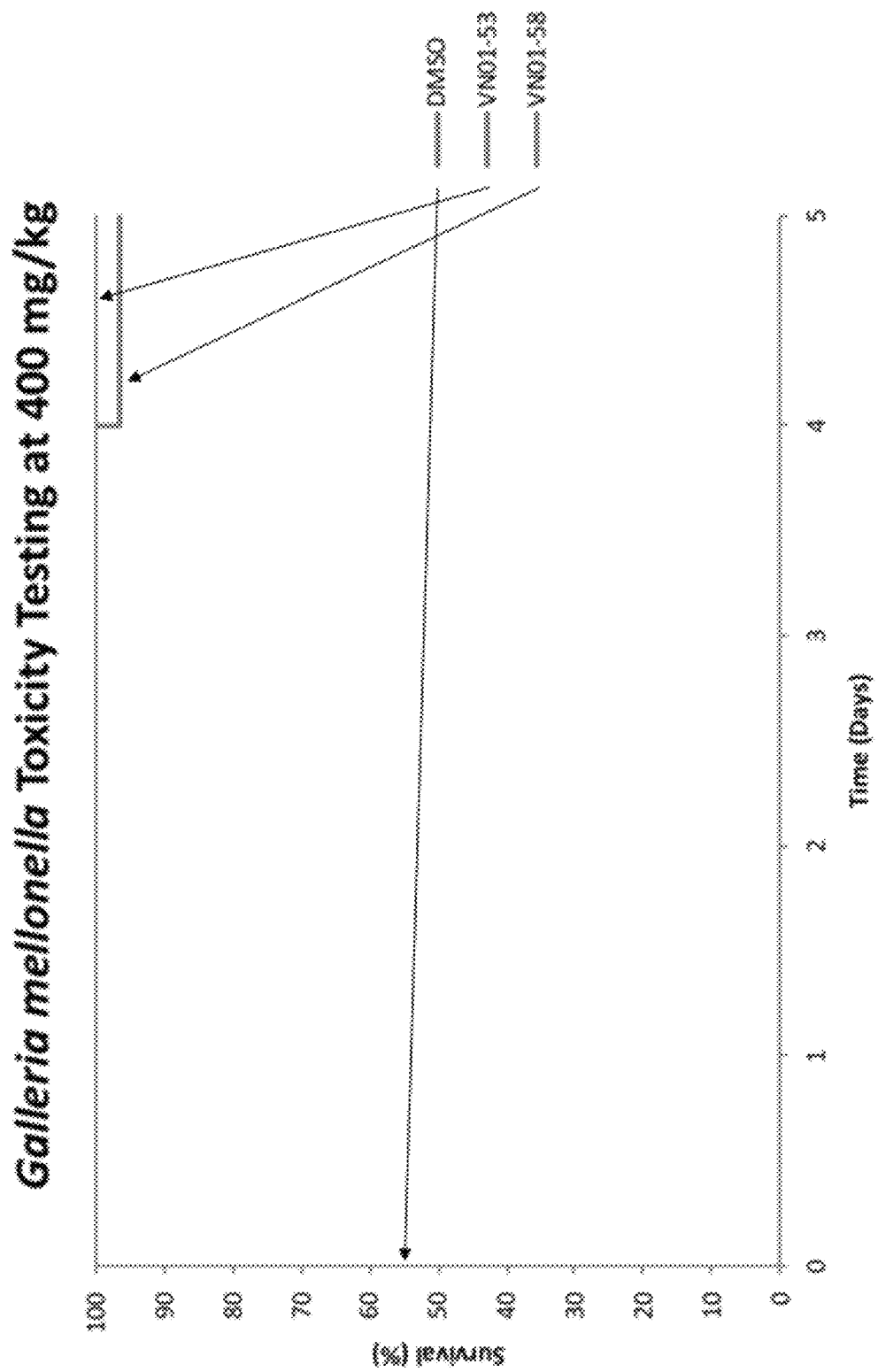

S. typhimurium grown in the presence of 10 µM of a representative disclosed compound, compound M4, for 24 hours showed no significant cell death over a 24-hour period (FIG. 5A). Toxicity was measured by drip plating and counting cfu/mL. Results of toxicity tests in Galleria mellonella larvae at 400 mg/kg, assessed over five days is shown in FIG. 5B.

Figure 6:
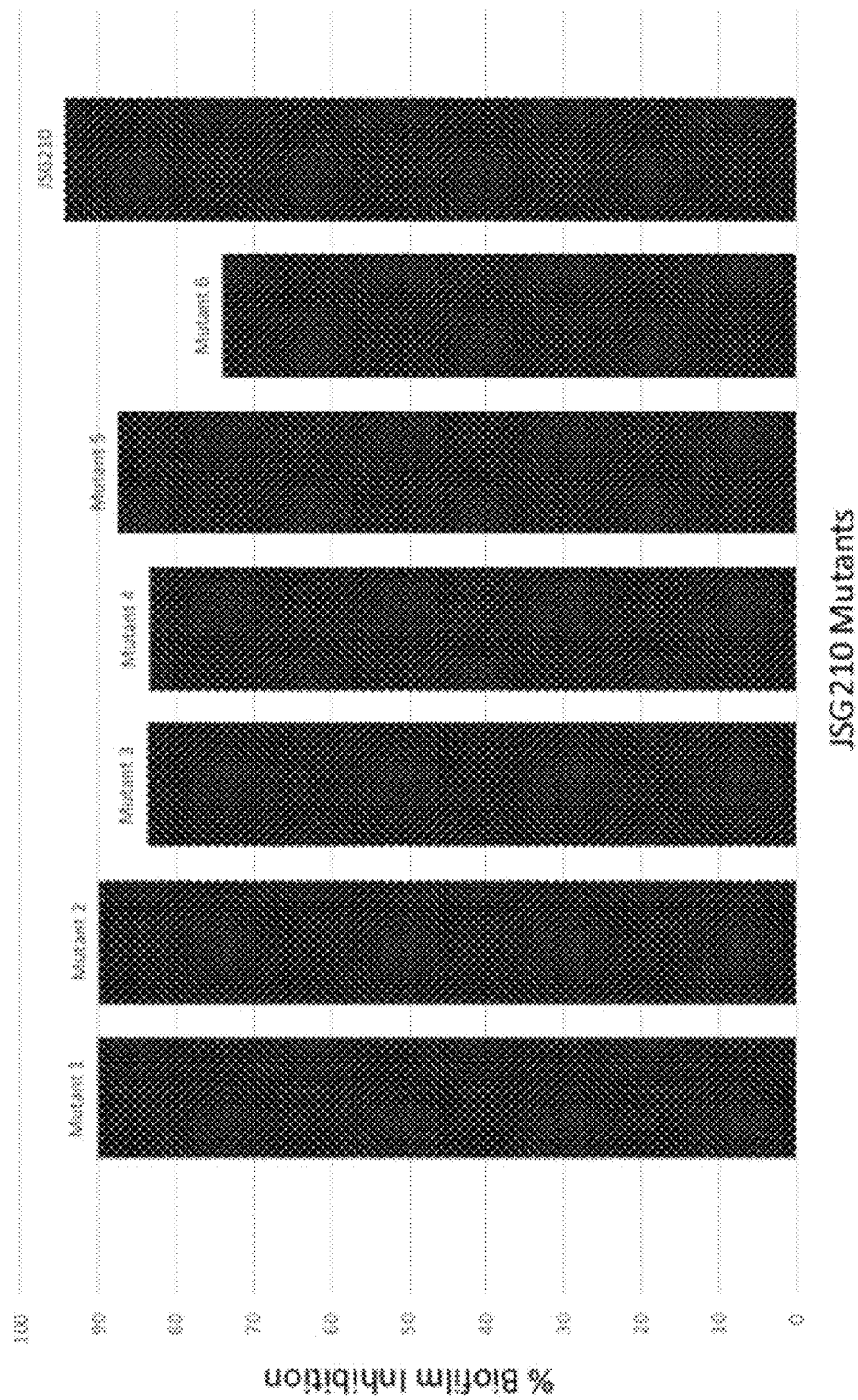
FIG. 6 shows representative data obtained from from Rapid Attachment Assay using newly generated JSG210 M4 mutants exposed to a representative disclosed compound, compound M4. The effects in these mutatns was compared to WT JSG210 control.

Mutants of S. typhimurium were generated by repeated exposure to representative disclosed compound, compound M4, to identify putative M4 target(s). FIG. 6 shows results from a Rapid Attachment Assay of JSG210 M4 mutants compared to WT JSG210. These strains are sequenced to identify genomic alterations.

A representative disclosed compound, compound M4, displayed significant biofilm dispersal and inhibition of biofilm formation in S. typhimurium, and no apparent toxicity to S. typhimurium at 10 µM or Galleria mellonella up to 400 mg/kg.

Example 2

Salmonella species are a frequent cause of food and water borne illness worldwide. They can cause a variety of disease syndromes, and are normally grouped into typhoidal and non-typhoidal species. Salmonella enterica serovar typhi is the causative agent of enteric fever and Salmonella enterica serovar Typhiumiurum is typically associated with intestinal distress, or salmonellosis (Truusalu, K., et al. Microb. Ecol. Health Dis., 2009, 16:180-187). Typhoidal and non-typhoidal strains of Salmonella have shown a remarkable ability to persist in a variety of environments, including harsh environments within the human body. One of these survival strategies centers around the ability of Salmonella to form biofilms on gallstones (Crawford, R W., et al. Proc. Natl. Acad. Sci. U. S. A., 2010, 107:4353-4358). Colonization of gallstones can then lead to chronic carriage of S. typhi, which allows for the dissemination of Salmonella through fecal shedding. Biofilms can be up to 1000-fold more resistant to antibiotic treatment than their planktonic counterparts, rendering typical antibiotic treatment regimens ineffective at eradicating chronic carriage of Salmonella (Stewart P S., et al. Lancet, 2001, 358:135-138; Donlan R M., et al. Clin. Microbiol. Rev., 2002:15, 167-193; Gonzalez, J F., et al. Sci. Rep., 2018, 8:222). Presently, chronic carriage of Salmonella is treated by invasive methods, which are not well suited to areas where Salmonella is prevalent (Gunn, J S., et al. Trends Microbiol., 2014, 22: 648-655). New treatment options for chronic carriage of Salmonella are needed, and compounds that perturb Salmonella biofilms could be a viable treatment option.

Figure 7:
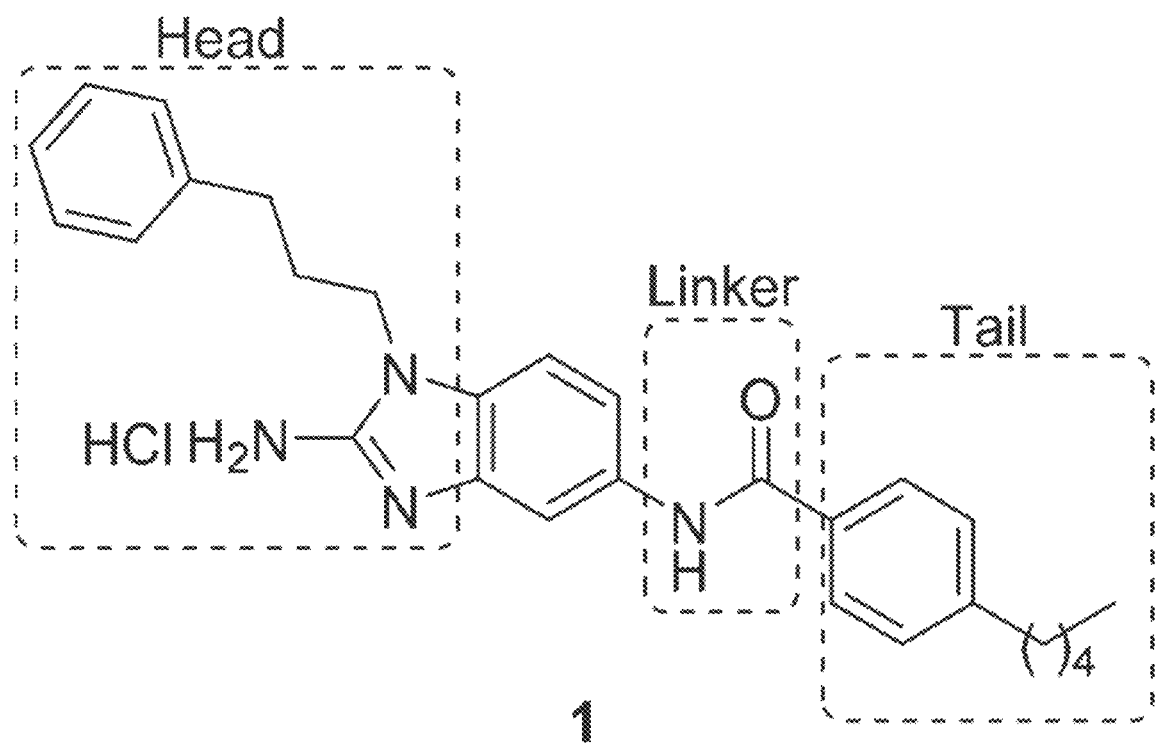
FIG. 7 shows the structure of regions of modification in Compound 1.

Recently, there have been reports of derivatized 2-aminoimidazoles (2-AIs) that inhibit S. typhimurium biofilm formation (Ermolat'ev, D S., et al. Angew. Chem., Int. Ed., 2010, 49:9465-9468; Steenackers, H P., et al. J. Med. Chem., 2011, 54:472-484; Steenackers, H P., et al. Bioorg. Med. Chem., 2011, 19:3462-3473; Robijns, S C., et al. FEMS Immunol. Med. Microbiol., 2012, 65:390-394; Steenackers, H., et al. Org. Biomol. Chem., 2014, 12:3671-3678; Trang, T T T., et al. Bioorg. Med. Chem., 2018, 26:1470-1480). As our group has been deeply involved in exploring the antibiofilm potential of 2-AIs, we were curious if there were 2-AI derivatives in our library, or derivatives of other nitrogen-dense heterocycles that we have assembled and assayed for their antibiofilm activities, that possessed activity against S. typhimurium. As S. typhi is a human-specific pathogen, reliable murine pathogenic serovars such as S. typhimurium have been used to model S. typhi infections, allowing for future in vivo testing (Wu, S., et al. J. Visualized Exp., 2010, (39):1947; Truusalu, K. et al. BMC Microbiol., 2008, 8:132). An initial library screen was performed for inhibitors of S. typhimurium biofilm formation and identified 2-aminobenzimidazole (2-ABI) compound 1 as one lead compound that returned an $IC_{50}$ value of 13.1±0.6 µM. 2-ABIs display a wide variety of biological activity including antibiotic activity against MRSA and MDR A. baumannii (Huigens, R W., 3rd, et al. Bioorg. Med. Chem., 2010, 18:663-674), antibiofilm activity against Gram-positive bacteria (Rogers, S A., et al. J. Am. Chem. Soc., 2009, 131:9868-9869), and the ability to potentiate β-lactam antibiotic activity against Mycobacterium smegmatis and M. tuberculosis (Nguyen, T V., et al. Angew. Chem., Int. Ed., 2017, 56:3940-3944). With this compound in hand, it was decided to probe the structure-activity relationship (SAR) of the 2-ABIs against S. typhimurium biofilms. The results of this SAR study of the 2-ABI scaffold are reported in this Example, focusing on three regions: the head region, the linker and the tail region (FIG. 7).

The first region of the molecule modified was the head region of the 2-ABI using a synthetic scheme (Scheme 1A) (Lindsey, E A., et al. MedChemComm, 2012, 3:1462-1465). Briefly, 4-fluoro-3-nitroaniline 2 was acylated with 4-pentylbenzoyl chloride in the presence of triethylamine and 4-dimethylaminopyrimidine (DMAP) in DCM for 16 hours at room temperature to yield compound 3. SNAr substitution of compound 3 with commercially available amines in refluxing ethanol for 16 hours yielded compounds 4a-n. Subsequent reduction of the nitro group with ammonium formate and 10% Pd/C in ethanol at reflux followed by cyclization with cyanogen bromide in DCM at room temperature yielded 2-ABIs 5a-n. The unsubstituted 2-ABI derivative, compound 5o, was prepared using a previously published method (Huigens, R W., 3rd, et al. Bioorg. Med. Chem., 2010, 18:663-674; Kikuchi, K., et al. Bioorg. Med. Chem., 2006, 14:6189-6196).

Three head group substitutions, n-octyl (5a), butyl phenyl (5b), and n-hexyl (5c) displayed improved activity (Table 1) over the parent compound. Isobutyl substitution (compound 5d) or substitution with tryptamine (5e) returned an $IC_{50}$ value between 10-15 µM, similar to that of parent compound 1 ($IC_{50}$ values were only quantified for compounds that had marked improvement over compound 1). Substitution with cyclopentyl (5g) or cyclohexyl rings (5h) returned slightly higher $IC_{50}$ values compared to the parent (15-20 µM). Shortening the phenyl chain to two methylenes also reduced activity, with compound 5i returning an $IC_{50}$ value of 20-40 µM (ESI†). Replacement of the phenyl ring on compound 5i with an imidazole (5j) ring also returned an $IC_{50}$ value of 20-40 µM. Alkyl chains with less than four carbon atoms (5k, 5l) or longer than eight carbon atoms (5m, 5n) reduced or completely abolished antibiofilm activity. Removal of the head group (compound 5o) from the 2-ABI lowers the $IC_{50}$ from 13.1±0.6 µM to 20-40 µM, demonstrating the necessity of the head group for biofilm inhibitory activity.

TABLE 1
IC$_{50}$ values of para 2-ABI, compounds 5a-h, and meta 2-ABI, compounds 9a-b. Full inhibition data can be found in the ESI
| Compound | R = | IC$_{50}$ (μM) |
|---|---|---|
| 5a |  | 6.66 ± 0.32 |
| 5b | 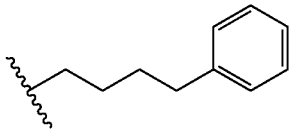 [SMILES: *CCCCc1ccccc1] | 9.59 ± 0.23 |
| 5c |  | 10.8 ± 0.56 |
| 1 | 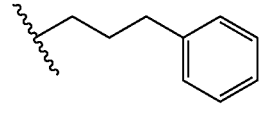 [SMILES: *CCCc1ccccc1] | 13.1 ± 0.6 |
| 5d | 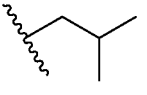 [SMILES: *CC(C)C] | 10-15 |
| 5e | 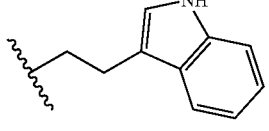 | 10-15 |
| 5f |  | 15-20 |
| 5g | 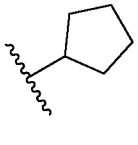 [SMILES: *C1CCCC1] | 15-20 |
| 5h | 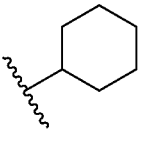 [SMILES: *C1CCCCC1] | 15-20 |
| 9a |  | 10-15 |
| 9b |  | 10-15 |
TABLE 2
IC$_{50}$ values of 2-ABIs with different tails, compounds 10a-n. Full inhibition data can be found in the ESI
| Compound | R = | IC$_{50}$ (μM) |
|---|---|---|
| 10a | 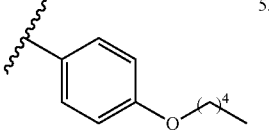 | 5.22 ± 0.11 |
| 10b | 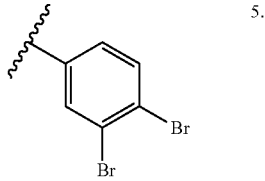 | 5.38 ± 0.79 |
| 10c | 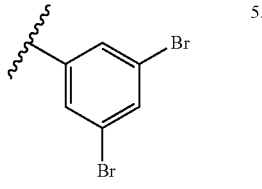 | 5.58 ± 0.21 |
| 10d | 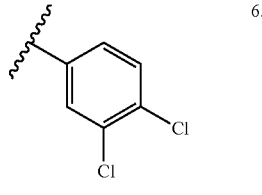 | 6.30 ± 1.29 |
| 1 | 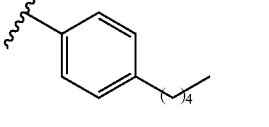 | 13.1 ± 0.6 |
| 10e | 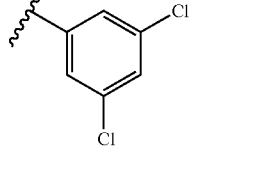 | 10-15 |
| 10f | 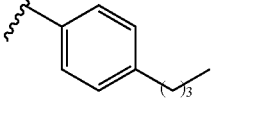 | 10-15 |
| 10g | 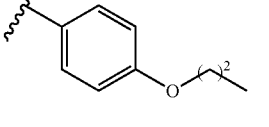 | 10-15 |
| 10h | 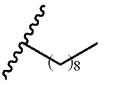 | 10-15 |

TABLE 2-continued

IC$_{50}$ values of 2-ABIs with different tails, compounds 10a-n.
Full inhibition data can be found in the ESI

| Compound | R = | IC$_{50}$ (μM) |
|---|---|---|
| 10i | (CH$_2$)$_9$ chain | 10-15 |
| 10j | 4-(OCH$_2$CH$_2$CH$_2$CH$_3$)phenyl | 15-20 |
| 10k | 4-propylphenyl | 15-20 |
| 10l | 4-pentylphenyl | 15-20 |
| 10m | 4-hexylphenyl | 15-20 |
| 10n | (CH$_2$)$_7$ chain | 15-20 |

Figure 8:
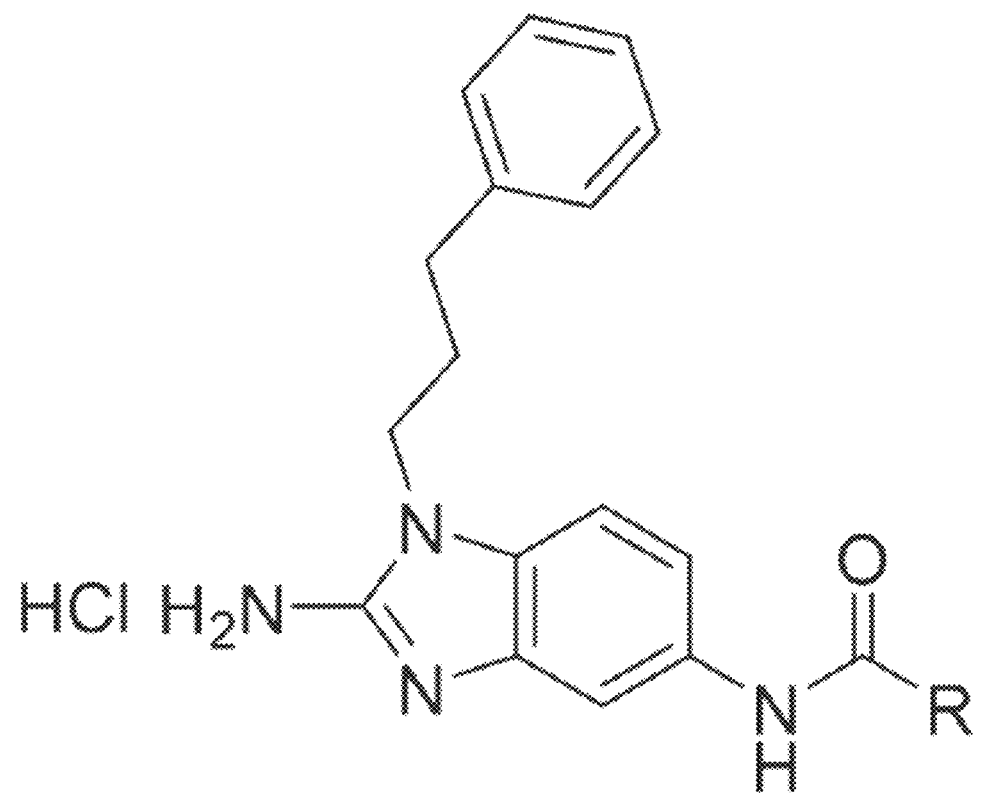
FIG. 8 shows the structure of compounds 10a-t with various tail substitutions.
Figure 9:
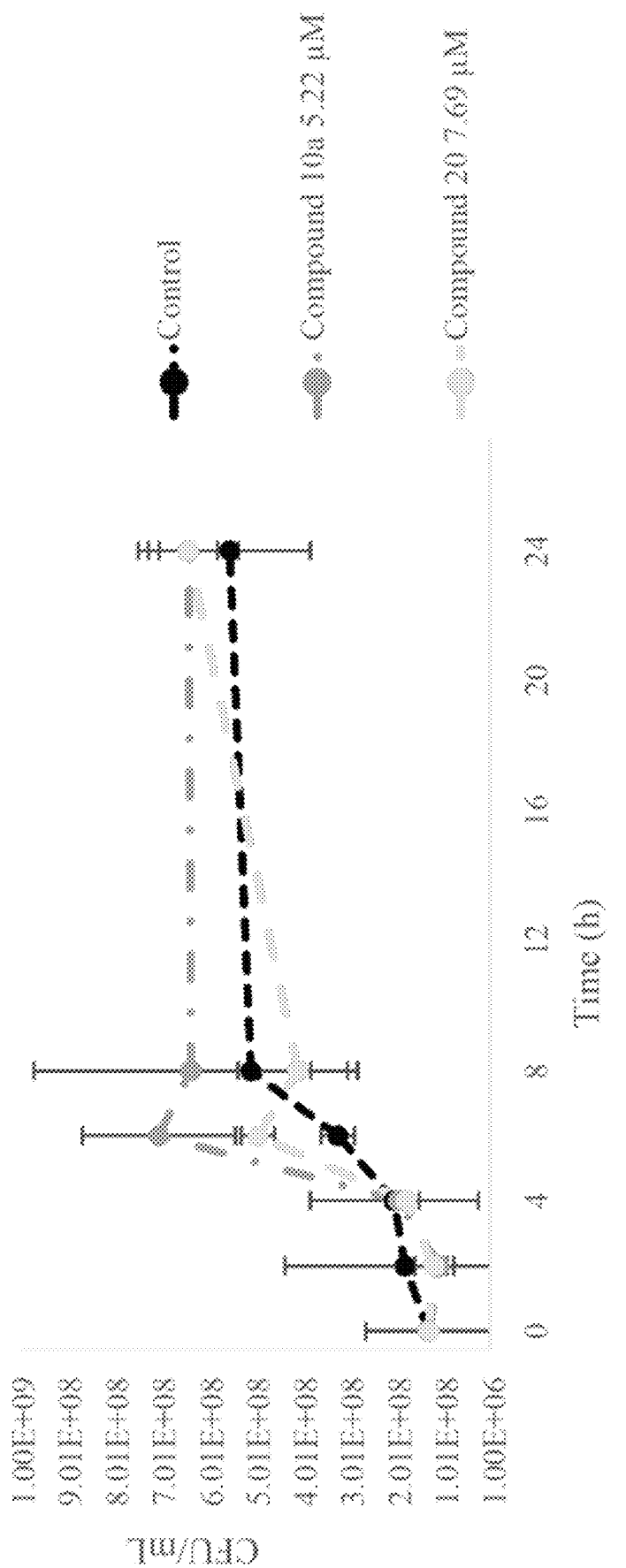
FIG. 9 shows growth curves for select compounds against S. typhimurium ATCC 14028

After investigating different head group substitutions in the para position relative to the amide, analogues with the head group substitution meta to the amide were prepared. The synthetic route to these compounds (Scheme 1B), is identical to that of the para analogues (Scheme 1A) except the starting material is 3-fluoro-4-nitroaniline 6. Compared to their para substituted counterparts, the meta analogues did not display a significant increase in activity (Table 1). Only the butyl analogue 9a (IC$_{50}$ 10-15 μM) displayed increased activity compared to butyl para analogue 5f (IC$_{50}$ 15-20 μM). n-Hexyl analogue 9b displayed almost identical activity to the para n-hexyl analogue 5c, returning an IC$_{50}$ of 10-15 μM. Methyl (9c), ethyl (9d), and isopropyl (9e) analogues all displayed IC$_{50}$ values of 20-40 μM (ESI†). After modifying the head region of the molecule, substitutions to the tail of the molecule were made in an effort to improve the antibiofilm ability of the parent compound. Previously, various 2-ABI derivatives with an identical head group to the parent compound 1 and various tails were prepared (FIG. 8) (Nguyen, T V., et al. Angew. Chem., Int. Ed., 2017, 56:3940-3944). As these compounds were readily available in our laboratory, their anti-*Salmonella* biofilm activity was investigated. Halogenation (10b, 10c and 10d) of the aromatic ring lowers the IC50 value when compared to a 4-pentylbenzoyl group, all returning IC$_{50}$ values of less than 7 μM (Table 2). The 3,5-dichloro analogue 10e displays lower activity compared to the other halogenated tails, but displays essentially equivalent activity to the parent compound 1. Addition of a pentoxybenzoyl group (10a) returns the lowest IC$_{50}$ observed, with an IC$_{50}$ of 5.22±0.11 μM. Although substituted benzoyl groups are favored in the most active compounds, removal of the aromatic ring in favor of a straight alkyl chain is tolerated as observed with nonanoyl (10h) and decanoyl (10i) tails. 4-Butylbenzoyl (10f), and 4-propoxybenzoyl (10g) tails all returned an IC50 value of 10-15 μM, similar to that of the parent compound (1) and the 3,5-dichlorobenzoyl compound (10e). Additional analogues were investigated, but all displayed lower activity in comparison to the parent compound. 4-Butoxybenzoyl (10j), 4-propylbenzoyl (10k), 4-hexylbenzoyl (10l), 4-heptylbenzoyl (10m), and octanoyl (10n) tails all returned IC50 values of 15-20 μM. 4-Ethylbenzoyl (10o) and hexanoyl (10p) tails returned IC$_{50}$ values between 20-40 μM (ESI†). Lastly, heptanoyl (10q), 4-octylbenzoyl (10r), undecanoyl (10s), and tridecanoyl (10t) tails returned IC$_{50}$ values of greater than 40 μM.

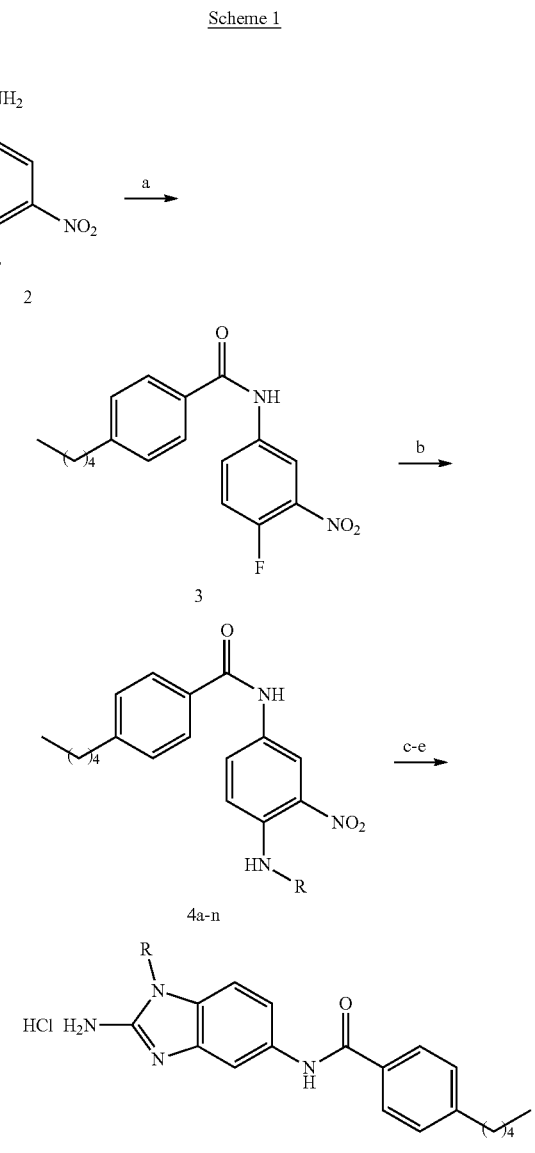

Scheme 1

-continued

B.

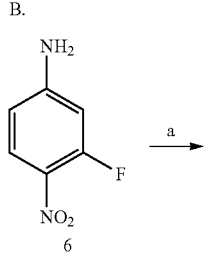
6

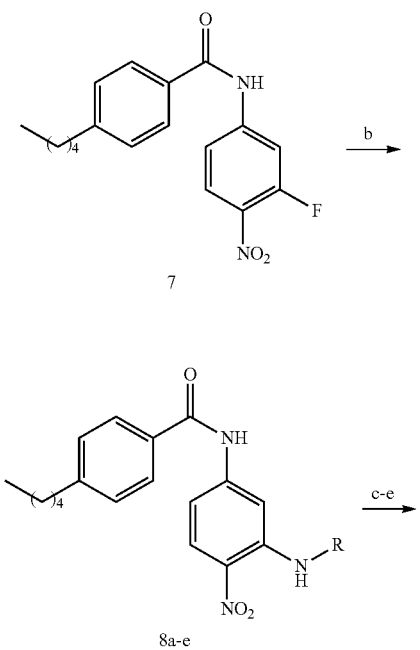
7

8a-e

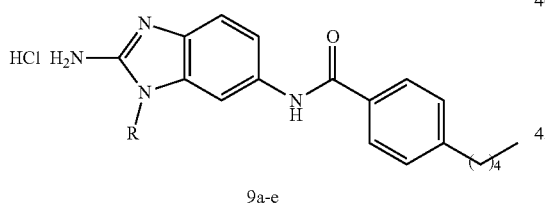
9a-e (A) Synthetic route to compounds 5a-n and
(B) synthetic route to compounds 9a-e:
(a) 4-pentylbenzoyl chloride, DMAP, Et3N, DCM, 16 h
(b) RNH2, EtOH, reflux, 16 h
(c) NH4HCO2, 10% Pd/C, EtOH, reflux, 3 h
(d) CNBr, DCM, 16 h
(e) HCl, MeOH.

The last region of the 2-ABIs that was modified was the linker region. The 2-ABIs previously synthesized (Huigens, R W., 3rd, et al. Bioorg. Med. Chem., 2010, 18:663-674; Rogers, S A., et al. J. Am. Chem. Soc., 2009, 131:9868-9869; Nguyen, T V., et al. Angew. Chem., Int. Ed., 2017, 56:3940-3944; Lindsey, E A., et al. MedChemComm, 2012, 3:1462-1465) that served as the basis for the 2-ABIs used in this study have featured an amide linkage, with the nitrogen in the amide connected to the 2-ABI head of the molecule. Previous studies on other 2-AI natural products have demonstrated the effect that modification of the amide moiety can have on a compound's ability to control bacterial behavior as well as its toxicity in C. elegans (Richards, J J.,  et al. J. Med. Chem., 2009, 52:4582-4585). With this in mind, 2-ABI derivatives were synthesized with a reverse amide moiety as well as a urea moiety replacing the amide. Compound 10d was chosen as the compound for further analog development due to its predicted reduced metabolic liabilities.

The synthesis of the reverse amide analogue (Scheme 2A) began by reacting 4-fluoro-3-nitrobenzoic acid with thionyl chloride in methanol at 0° C., warming to room temperature overnight to yield the methyl ester 12. Compound 12 was then reacted with 3-phenyl-1-propylamine in ethanol at reflux to yield 13. Reduction of the nitro group followed by cyclization with cyanogen bromide in DCM at room temperature yielded the 2-ABI 14. Lastly, saponification of the methyl ester with sodium hydroxide in 1:1 MeOH/H$_2$O followed by EDC coupling of the carboxylic acid with 3,4-dichloroaniline delivered the reverse amide 2-ABI 15.

Synthesis of the urea analogue (Scheme 2B) began with the Boc protection of 4-fluoro-3-nitroaniline, yielding 16. Compound 16 was then reacted with 3-phenyl-1-propylamine to yield the diaminobenzene 17. Reduction of the nitro group using ammonium formate and 10% Pd/C in ethanol at reflux followed by cyclization with cyanogen bromide in DCM at room temperature yielded Boc-protected 2-ABI 18. Alloc protection of the 2-ABI head proceeded smoothly utilizing scandium(III) triflate as a Lewis-acid catalyst in DCM overnight at room temperature, yielding alloc protected 2-ABI 19. Boc deprotection of compound 20 followed by coupling with 3,4-dichloroaniline using triphosgene yielded the Alloc protected 2-ABI urea. Finally, Alloc deprotection with Pd(PPh$_3$)$_4$ and NaBH 4 yielded the target 2-ABI urea 20.

Scheme 2

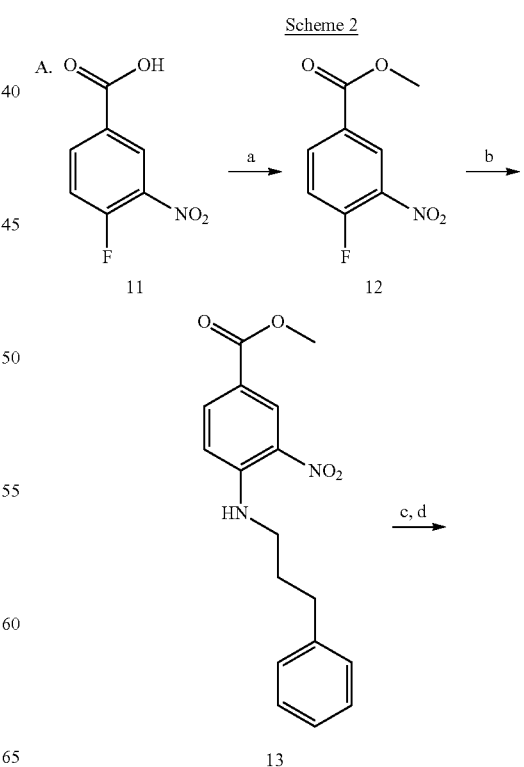

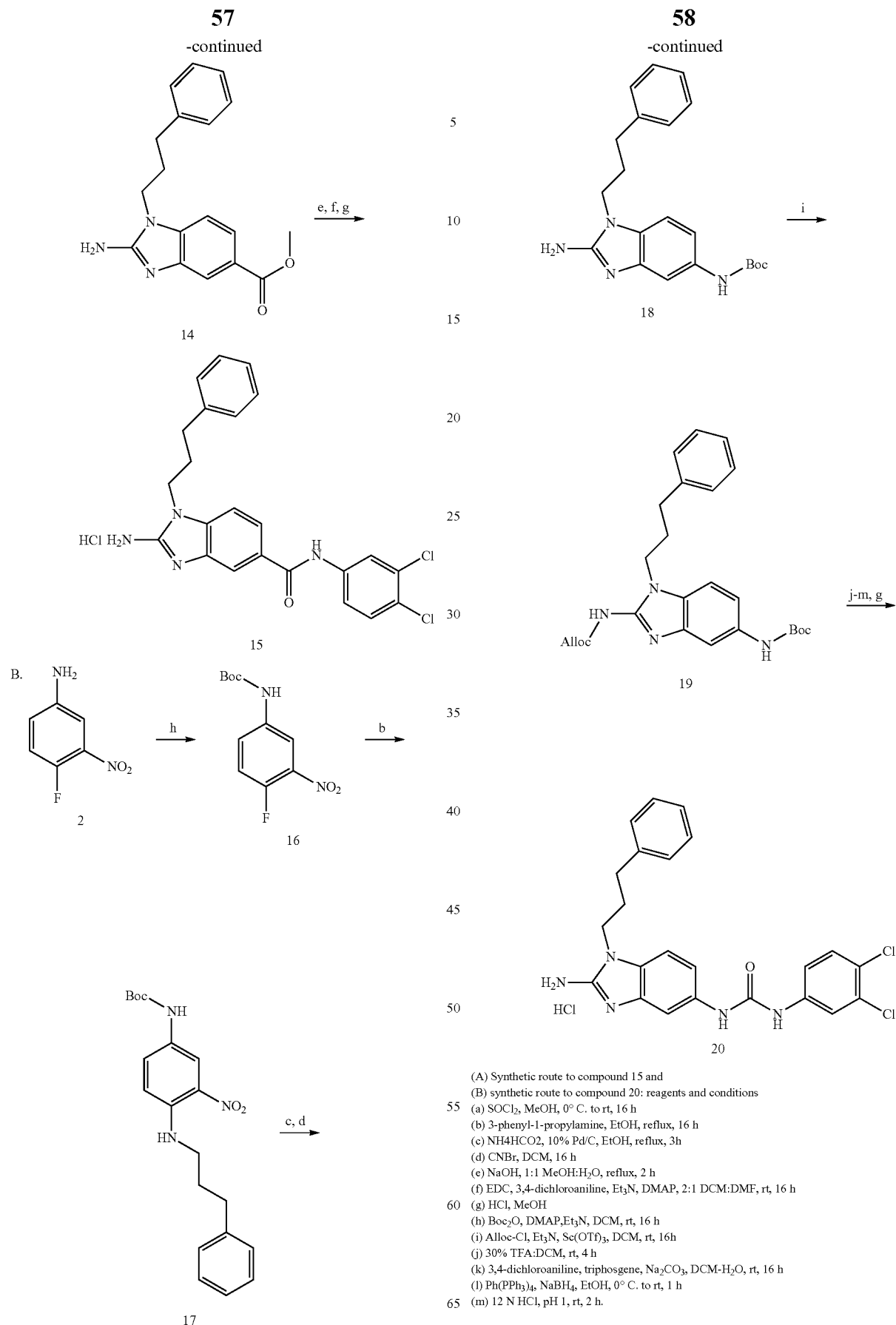

While the reverse amide analogue 15 displayed a twofold greater $IC_{50}$ (12.6±1.8 µM) than that of the parent compound 10d, the urea analogue 20 displayed only a slight reduction in $IC_{50}$ value from 6.30±1.29 to 7.69±0.25 µM, demonstrating that the linker group of the 2-ABIs can be modified while retaining biofilm inhibitory activity against *S. typhimurium*. Additionally, compounds 10a and 20 showed no toxicity to planktonic bacterial growth at their $IC_{50}$ values, indicating that they are nontoxic biofilm inhibitors (ESI†).

EXPERIMENTAL

All reagents used for chemical synthesis were purchased from commercially available sources and used without further purification. Chromatography was performed using 60 Å mesh standard grade silica gel from Sorbtech. NMR solvents were obtained from Cambridge Isotope Laboratories and used as is. All 1H NMR (300 or 400 MHz) and $^{13}C$ NMR (75, 100, or 175 MHz) spectra were recorded at 25° C. on Varian Mercury spectrometers. Chemical shifts (δ) are given in parts per million relative to tetramethylsilane or the respective NMR solvent; coupling constants (J) are in hertz (Hz). Abbreviations used are s, singlet; brs, broad singlet; d, doublet; dd, doublet of doublets; t, triplet; dt, doublet of triplets; m, multiplet. Mass spectra were obtained at the NCSU Department of Chemistry Mass Spectrometry Facility. Infrared spectra were obtained on an FT/IR-4100 spectrophotometer (vmax in $cm^{-1}$). UV absorbance was recorded on a Genesys 10 scanning UV/visible spectrophotometer (λmax in nm). The purities of the tested compounds were all verified to be >95% by LC-MS analysis on a Shimadzu LC-MS 2020 with Kinetex, 2.6 mm, C18 50×2.10 mm.

Procedure to Determine the Inhibitory Effect of Test Compounds on *Salmonella typhimurium* ATCC14028 Biofilms: Inhibition assays were performed by taking an overnight culture of *S. typhimurium* ATCC14028 in tryptic soy broth (TSB, BD™ Bacto™) and subculturing it at an OD600 of 0.08 into 1:20 TSB:Water. Stock solutions of predetermined concentrations of the test compounds were then made in 1 mL of bacterial culture. The resulting bacterial suspension was aliquoted (100 µL) into the wells of a 96-well PVC microtiter plate. Sample plates were then incubated for 24 h at 30° C. After incubation, the medium was discarded from the wells and the plates were washed thoroughly with water. Plates were then stained with 110 µL of 0.1% solution of crystal violet (CV) and then incubated at ambient temperature for 30 min. Plates were washed with water again and the remaining stain was solubilized with 200 µL of 95% ethanol. A sample of 125 µL of solubilized CV stain from each well was transferred to the corresponding wells of a polystyrene microtiter dish. Biofilm inhibition was quantitated by measuring the OD540 of each well in which a negative control lane wherein no biofilm was formed served as a background and was subtracted out.

Growth Curves: *S. typhimurium* was grown overnight in TSB, and this culture was used to inoculate fresh 1:20 TSB ($OD_{600}$=0.08). Inoculated medium was aliquoted (3 mL) into culture tubes, and compound was added, with untreated inoculated medium serving as the control. Tubes were incubated at 30° C. with shaking. Samples were taken at 2, 4, 6, 8, and 24 h time points, serially diluted in fresh 1:20 TSB, and plated on nutrient agar. Plates were incubated at 37° C. overnight in stationary conditions, and the number of colonies was enumerated.

Complete 2-ABI Library Inhibition Data Against *S. typhimurium* 14028

| Compound | R = | $IC_{50}$ (µM) |
|---|---|---|
| 5a | (CH₂)₇CH₃ branched | 6.66 ± 0.32 |
| 5b | -(CH₂)₄-phenyl | 9.59 ± 0.23 |
| 5c | (CH₂)₅ branched | 10.8 ± 0.56 |
| 1 | -(CH₂)₂-phenyl | 13.1 ± 0.6 |
| 5d | isobutyl | 10-15 |
| 5e | -(CH₂)₂-(3-indolyl) | 10-15 |
| 5f | (CH₂)₃ branched | 15-20 |
| 5g | cyclopentyl | 15-20 |

-continued
1. 5a-n
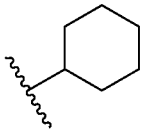 [SMILES: *C1CCCCC1]
9a-e
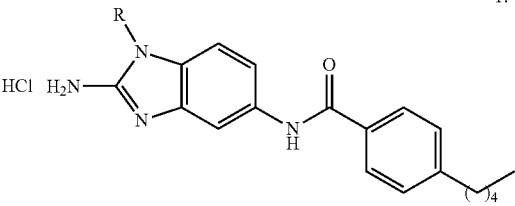
| Compound | R = | IC$_{50}$ (μM) |
|---|---|---|
| 5h | 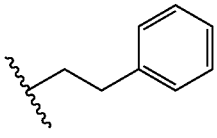 [SMILES: *CCc1ccccc1] cyclohexyl | 15-20 |
| 5i | 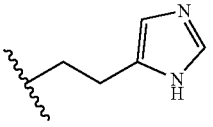 [SMILES: *CCc1cnc[nH]1] phenethyl | 20-40 |
| 5j | 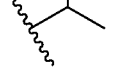 imidazole-propyl | 20-40 |
| 5o | H | 20-40 |
| 5k | 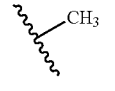 isobutyl | 20-40 |
| 5l | CH$_3$ | >40 |
| 5m | (CH$_2$)$_9$CH$_3$ | >50 |
| 5n | (CH$_2$)$_{11}$CH$_3$ | >50 |
| 9a | (CH$_2$)$_3$CH$_3$ | 10-15 |
| 9b | (CH$_2$)$_5$CH$_3$ | 10-15 |
-continued
1. 5a-n
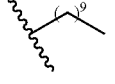
9a-e
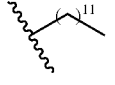
| Compound | R = | IC$_{50}$ (μM) |
|---|---|---|
| 9c | CH$_3$ | 20-40 |
| 9d | (CH$_2$)CH$_3$ | 20-40 |
| 9e | 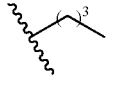 isopropyl | 20-40 |
10a-t
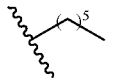
| Compound | R = | IC$_{50}$ (μM) |
|---|---|---|
| 10a |  4-butoxyphenyl | 5.22 ± 0.11 |
| 10b | 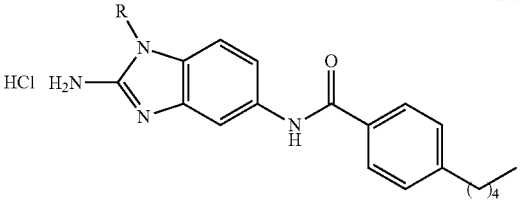 3,4-dibromophenyl | 5.38 ± 0.79 |

-continued 10a-t

| Compound | R = | IC$_{50}$ (μM) |
|---|---|---|
| 10c | 3,5-dibromophenyl | 5.58 ± 0.21 |
| 10d | 3,4-dichlorophenyl | 6.30 ± 1.29 |
| 1 | 4-butylphenyl | 13.1 ± 0.6 |
| 10e | 3,5-dichlorophenyl | 13.3 ± 0.49 |
| 10f | 4-propylphenyl | 10-15 |
| 10g | 4-(2-ethoxy)phenyl | 10-15 |
| 10h | -(CH$_2$)$_8$CH$_3$ | 10-15 |
| 10i | -(CH$_2$)$_9$CH$_3$ | 10-15 |

-continued 10a-t

| Compound | R = | IC$_{50}$ (μM) |
|---|---|---|
| 10j | 4-(propoxy)phenyl | 15-20 |
| 10k | 4-ethylphenyl | 15-20 |
| 10l | 4-pentylphenyl | 15-20 |
| 10m | 4-hexylphenyl | 15-20 |
| 10n | -(CH$_2$)$_7$CH$_3$ | 15-20 |
| 10o | 4-methylphenyl | 20-40 |

| Compound | R = | IC$_{50}$ (μM) |
|---|---|---|
| 10p | (CH$_2$)$_5$ | 20-40 |
| 10q | (CH$_2$)$_6$ | >40 |
| 10r | -C$_6$H$_4$-(CH$_2$)$_7$- | >50 |
| 10s | (CH$_2$)$_{10}$ | >50 |
| 10t | (CH$_2$)$_{12}$ | >50 |

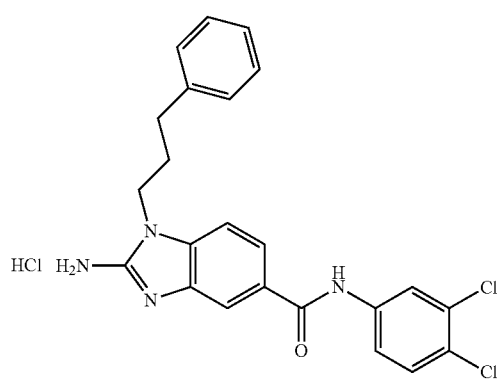 [SMILES: Cl ; Nc1nc2cc(C(=O)Nc3ccc(Cl)c(Cl)c3)ccc2n1CCCc1ccccc1]

15

20

| Compound | IC$_{50}$ (μM) |
|---|---|
| 15 | 12.6 ± 1.8 |
| 20 | 7.69 ± 0.25 |

General Synthetic Procedures

General synthetic procedure for aniline acylation (Compounds 3, 7): To a solution of nitroaniline (1.0 g, 6.41 mmol) in anhydrous Dichloromethane (35 mL), was added DMAP (0.782 g, 1.0 mmol), and 4-pentylbenzoyl chloride (1.69 mL, 8.32 mmol) dropwise. The reaction was stirred under N2 for 16 hours, after which it was washed with H2O (3×100 mL), saturated aqueous NaHCO3 (2×100 mL), and saturated aqueous NaCl (1×100 mL). It was then dried with sodium sulfate and purified on silica gel, using EtOAc/Hexanes (30%) as the eluting solvent.

General synthetic procedure for SNAr substitution (Compounds 4a-n, 8a-e, 13, 17): Compounds 3, 7, 12, or 16 were added to a round bottom flask and dissolved in ethanol (1.0g, 0.5 M). To this mixture the corresponding amine (3-5 equivalents) was added dropwise. The reaction mixture was then heated to reflux and allowed to stir for 16 hours. The mixture was then cooled to room temperature. Water was added to the reaction mixture, causing the product to precipitate out of solution. This mixture was then cooled to 0° C. The product was then filtered and washed with cold water. The solid was then dried under high vacuum overnight.

General procedure for the 2-ABI nitro reduction and cyclization (Compounds 5a-n, 9a-e, 14, 18): The appropriate nitro-compound was dissolved in ethanol (1.0 g, 0.4 M), and 10% Pd/C (0.1 g) was added to the mixture. The reaction mixture was then heated to reflux. Ammonium formate was then dissolved in ethanol and added dropwise to the reaction mixture which was allowed to stir until completion, via TLC analysis. The mixture was then cooled to room temperature, and quickly filtered through a pad of celite which was washed with dichloromethane. The crude product was then placed under nitrogen, and solid cyanogen bromide (10 eq) was added to the crude product and allowed to stir overnight. The reaction mixture was then concentrated and purified using column chromatography (1-5% MeOH/NH3-DCM). Methanol supplemented with 12N HCl was added to the product forming the HCl salt, which was then dried under high vacuum overnight.

General synthetic procedure for methyl ester synthesis (Compound 12): To a solution of 4-fluoro-3-nitrobenzoic acid (2.00 g, 10.8 mmol) in MeOH (20 mL) at 0° C. was added thionyl chloride (2.35 mL, 32.4 mmol) dropwise, and the reaction mixture was allowed to stir overnight. After completion, the reaction was extracted with diluted in water and extracted with ethyl acetate (3×20 mL). The combined organic layers were then washed with saturated sodium bicarbonate (2×30 mL). The organic layer was then dried with sodium sulfate, and the product was concentrated to yield the product with no further purification.

General synthetic procedure for saponification followed by EDC coupling (Compound 15): 2-ABI methyl ester (compound 14, 0.200 g, 0.645 mmol) was dissolved in a 1:1 mixture of MeOH:H2O (20 mL) to which a 5M solution of sodium hydroxide (10 mL) was added. The mixture was then heated to reflux while stirring for 16 hours. After completion, the methanol was removed under reduced pressure. The remaining aqueous solution was then cooled to 0° C., and 12N HCl was added until the pH reached ~2. The resulting precipitate was then isolated using vacuum filtration and allowed to dry under high vacuum for 2 hours. A solution of carboxylic acid (0.107 g, 0.362 mmol), EDC (0.073, 0.471 mmol), DMAP (0.044 g, 0.362 mmol), and 3,4-dichloroaniline (0.176 g, 1.09 mmol) was made in a 5:1 mixture of DCM:DMF. The reaction was allowed to stir for 16 hours at room temperature. After completion, the DCM was removed under reduced pressure. The remaining solution was then dissolved in ethyl acetate (25 mL) washed with water (1×40 mL), saturated sodium bicarbonate (2×15 mL), and brine (1×20 mL). The organic layer was then dried over sodium sulfate and concentrated under reduced pressure to yield the crude product. The crude product was then purified using flash chromatography (0.5-5% MeOH—NH3/DCM). Methanol supplemented with 12N HCl was added to the product forming the HCl salt, which was then dried under high vacuum overnight. General synthetic procedure for aniline boc protection (Compound 16): To a solution of 4-fluoro-3-nitroaniline (5.0 g, 32.03 mmol) in anhydrous THF (150 mL) was added triethylamine (44.7 mL, 320.28 mmol) and DMAP (0.039 g, 0.32 mmol). Di-tert-butyl dicarbonate (10.49 g, 48.4 mmol) was added, and solution was stirred at room temperature overnight (16 h). The solvent was removed under reduced pressure, and the crude product was dissolved in ethyl acetate (100mL), and washed with 1N HCl (3×100 mL), saturated sodium bicarbonate (3×100 mL), and brine (1×100 mL). The organic layer was dried over sodium sulfate. The solvent was removed under reduced pressure, and the crude product was purified via flash chromatography (5-20% ethyl acetate/hexanes).

General synthetic procedure for 2-ABI alloc protection (Compound 19): Compound 18 (1.15 g, 3.14 mmol) was placed under an inert atmosphere and dissolved in DCM (25 mL). To the reaction mixture was added 0.05 equivalents of Sc(OTf)3 and triethylamine triethylamine (0.482 mL, 3.45 mmol). The reaction mixture was cooled to 0° C. Allyl chloroformate (0.365 mL, 3.45 mmol) was slowly added dropwise to the reaction mixture. The reaction mixture was stirred at 0° C. for 20 min and allowed to warm up to room temperature overnight. The solvent was removed under reduced pressure, and the crude product was dissolved in DCM (100 mL). The organic layer was washed with saturated sodium bicarbonate (3×100 mL), and brine (1×100 mL). The organic layer was dried over sodium sulfate. The solvent was removed under reduced pressure, and the crude product was purified via flash chromatography (1-5% MeOH—NH3/DCM).

General synthetic procedure for Boc deprotection, urea coupling followed by alloc deprotection (Compound 20): Compound 19 (0.123 g, 0.273 mmol) was dissolved in 30% TFA/DCM under an inert atmosphere at 0° C. The reaction was allowed to stir for 4 h, and upon completion via TLC analysis, the solvent was then removed under reduced pressure. The crude product was dissolved in DCM, and washed with saturated sodium bicarbonate (3×100 mL). The organic layer was dried over sodium sulfate, and the solvent was removed under reduced pressure. The crude product was then dissolved in dichloromethane (10 mL) to which sodium carbonate (0.046g, 0.434 mmol) and water (5 mL) was added and the mixture was allowed to stir for 10 minutes at room temperature. A solution of triphosgene (0.027g, 0.089 mmol) in DCM (5 mL) was added to the reaction mixture. After allowing the mixture to stir for 1 hour, 3,4-dichloroaniline (0.088 g, 0.542 mmol) in DCM (1 mL) was added dropwise to the reaction mixture. The reaction was then allowed to stir for 16 hours at room temperature. Following the completion of the reaction, the product was extracted with dichloromethane (15 mL) and washed with water (2×20 mL) and brine (1×20 mL). The crude mixture was then purified with flash chromatography (0.5-1.5% MeOH—NH3/DCM) to yield the product. After allowing the product to dry under high vacuum for 2 hours, the alloc protected urea (0.023 g, 0.427 mmol) was then placed under nitrogen and dissolved in ethanol (10 mL) at 0° C. Next, tetrakis (triphenylphosphine)palladium (0) (0.0001 g, 0.0001 mmol) and sodium borohydride (0.003 g, 0.085 mmol) were added to the reaction mixture and allowed to stir for 1 hour while warming to room temperature. The reaction was then acidified to pH 2.5-3 using 12 N HCl, and the reaction was allowed to stir for 4 h. After completion, the reaction was extracted with 1:1 EtOAC/Hex (2×20 mL). The combined organic layers were washed with water (20 mL), saturated NaHCO3 (20 mL), brine (20 mL), dried (MgSO4) and concentrated under reduced pressure. The residue was then purified using flash chromatography (1-5% MeOH—NH3/DCM) to yield the desired product. Methanol supplemented with 12N HCl was added to the product forming the HCl salt, which was then dried under high vacuum overnight.

N-(2-Amino-1-phenethyl-1H-benzo[d]imidazol-5-yl)-4-pentylbenzamide hydrochloride (1): Compound was synthesized using previously reported methods (Lindsey, E A, et al. MedChemComm, 2012, 3:1462-1465).

N-(2-Amino-1-octyl-1H-benzo[d]imidazol-5-yl)-4-pentylbenzamide hydrochloride (5a): Compound was synthesized using previously reported methods (Lindsey, E A, et al. MedChemComm, 2012, 3:1462-1465).

N-(2-Amino-1-(4-phenylbutyl)-1H-benzo[d]imidazol-5-yl)-4-pentylbenzamide hydrochloride (5b): Compound was synthesized using previously reported methods (Lindsey, E A, et al. MedChemComm, 2012, 3:1462-1465).

N-(2-Amino-1-hexyl-1H-benzo[d]imidazol-5-yl)-4-pentylbenzamide hydrochloride (5c): Compound was synthesized using previously reported methods (Lindsey, E A, et al. MedChemComm, 2012, 3:1462-1465).

N-(1-(2-(1H-Indol-3-yl)ethyl)-2-amino-1H-benzo[d]imidazol-5-yl)-4-pentylbenzamide hydrochloride (5e): Compound was synthesized using previously reported methods (Lindsey, E A, et al. MedChemComm, 2012, 3:1462-1465).

N-(2-Amino-1-butyl-1H-benzo[d]imidazol-5-yl)-4-pentylbenzamide hydrochloride (5f): Compound was synthesized using previously reported methods (Lindsey, E A, et al. MedChemComm, 2012, 3:1462-1465).

N-(2-Amino-1-cyclopentyl-1H-benzo[d]imidazol-5-yl)-4-pentylbenzamide hydrochloride (5g): Compound was synthesized using previously reported methods (Lindsey, E A, et al. MedChemComm, 2012, 3:1462-1465).

N-(2-Amino-1-cyclohexyl-1H-benzo[d]imidazol-5-yl)-4-pentylbenzamide hydrochloride (5h): Compound was synthesized using previously reported methods (Lindsey, E A, et al. MedChemComm, 2012, 3:1462-1465).

N-(2-Amino-1-isopropyl-1H-benzo[d]imidazol-5-yl)-4-pentylbenzamide hydrochloride (5k): Compound was synthesized using previously reported methods (Lindsey, E A, et al. MedChemComm, 2012, 3:1462-1465).

N-(2-Amino-1-methyl-1H-benzo[d]imidazol-5-yl)-4-pentylbenzamide hydrochloride (5l): Compound was synthesized using previously reported methods (Lindsey, E A, et al. MedChemComm, 2012, 3:1462-1465).

N-(2-Amino-1-dodecyl-1H-benzo[d]imidazol-5-yl)-4-pentylbenzamide hydrochloride (5n): Compound was synthesized using previously reported methods (Lindsey, E A, et al. MedChemComm, 2012, 3:1462-1465).

N-(2-Amino-1H-benzo[d]imidazol-5-yl)-4-pentylbenzamide hydrochloride (5o): Compound was synthesized using previously reported method (Huigens, 3rd, R W, et al. Bioorg. Med. Chem., 2010, 18:663-674).

N-(2-Amino-1-(3-phenylpropyl)-1H-benzo[d]imidazol-5-yl)-4-pentoxybenzamide hydrochloride (10a): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)-3,4-dibromobenzamide hydrochloride (10b): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)-3,5-dibromobenzamide hydrochloride (10c): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)-3,4-dichlorobenzamide hydrochloride (10d): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)-3,5-dichlorobenzamide hydrochloride (10e): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)-4-butylbenzamide hydrochloride (10f): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)-4-propoxybenzamide hydrochloride (10g): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-y0decanamide hydrochloride (10h): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yhundecanamide hydrochloride (10i): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)-4-butoxybenzamide hydrochloride (10j): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)-4-propylbenzamide hydrochloride (10k): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)-4-hexylbenzamide hydrochloride (10l): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)-4-heptylbenzamide hydrochloride (10m): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)nonanamide hydrochloride (10n): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)-4-ethylbenzamide hydrochloride (10o): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)heptanamide hydrochloride (10p): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)octanamide hydrochloride (10q): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yl)-4-octylbenzamide hydrochloride (10r): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yhdodecanamide hydrochloride (10s): Compound was synthesized using previously reported methods (Nguyen, T V, aa et al. Angew. Chem. Int. Ed., 2017, 56:3940-3944).

N-(2-Amino-1-(3-phenylpropyl)-1H-benzo[d]imidazol-5-yhtetradecanamide hydrochloride (10t): Compound was synthesized using previously reported methods (Nguyen, T V, aa et al. Angew. Chem. Int. Ed., 2017, 56:3940-3944).

Methyl 4-fluoro-3-nitrobenzoate (12): Compound was synthesized using previously reported methods (Gaugaz, F Z, et al. ChemMedChem, 2014, 9:2227-2232).

Methyl 3-nitro-4-((3-phenylpropyl)amino)benzoate (13): Compound was synthesized using previously reported methods (Nguyen, T V, aa et al. Angew. Chem. Int. Ed., 2017, 56:3940-3944; Selvaraju, M, et al. J. Org. Chem., 2016, 81:8867-8875).

Methyl 2-amino-1-(3-phenylpropyl)-1H-benzo[d]imidazole-5-carboxylate (14): Compound was synthesized using previously reported methods (Nguyen, T V, aa et al. Angew. Chem. Int. Ed., 2017, 56:3940-3944; Selvaraju, M, et al. J. Org. Chem., 2016, 81:8867-8875).

tert-Butyl (4-fluoro-3-nitrophenyl)carbamate (16): Compound was synthesized using previously reported methods (Nguyen, T V, aa et al. Angew. Chem. Int. Ed., 2017, 56:3940-3944)

tert-Butyl (3-nitro-4-((3-phenylpropyl)amino)phenyl)carbamate (17): Compound was synthesized using previously reported methods (Nguyen, T V, aa et al. Angew. Chem. Int. Ed., 2017, 56:3940-3944).

tert-Butyl (2-amino-1-(3-phenylpropyl)-1H-benzo[d]imidazol-5-yl)carbamate (18): Compound was synthesized using previously reported methods (Nguyen, T V, aa et al. Angew. Chem. Int. Ed., 2017, 56:3940-3944).

Compound Characterization

N-(4-(Isobutylamino)-3-nitrophenyl)-4-pentylbenzamide (4d): The title compound was synthesized from 3 following the general procedure to afford 4d as a red solid (35%). 1H NMR (300 MHz, CDCl3) δ 8.70 (brs, 1H), 8.24 (d, J=2.4 Hz, 1H), 8.06 (t, J=4.8 Hz, 1H), 7.79 (d, J=8.4 Hz, 3H), 7.16 (d, J=8.1 Hz, 2H), 6.70 (d, J=8.7 Hz, 1H), 3.04 (t, J=6.0 Hz, 2H), 2.58 (t, J=7.2 Hz, 2H), 1.94 (m, J=6.6 Hz, 1H), 1.56 (m, 2H), 1.30 (m, 4H), 1.02 (d, J=6.9 Hz, 6H), 0.81 (t, J=6.8 Hz, 3H) ppm; 13C NMR (100 MHz, CDCl3) δ 166.5, 147.3, 143.4, 131.6, 131.5, 130.4, 128.6, 127.3, 126.5, 118.7, 114.1, 50.8, 35.8, 31.5, 30.8, 28.0, 22.5, 20.4, 14.0 ppm; UV (λmax nm) 296; IR vmax (cm−1) 3257, 2970, 1666, 1514, 800; HRMS (ESI) calcd for C22H29N3O3 [M+H]+ 384.2282, found 384.2279.

N-(4-((2-(1H-Imidazol-5-yl)ethyl)amino)-3-nitrophenyl)-4-pentylbenzamide (4j): The title compound was synthesized from 3 following the general procedure to afford 4j as a red solid (53%). 1H NMR (400 MHz, DMSO-d6) δ 10.30 (s, 1H), 8.69 (s, 1H), 8.23 (brs, 1H), 7.94 (m, S42 3H), 7.60 (s, 1H), 7.32 (d, J=8.0 Hz, 2H), 7.12 (d, J=9.2 Hz, 1H), 6.93 (brs, 1H), 3.59 (m, 2H), 3.48 (brs, 3H), 2.88 (m, 2H), 2.63 (m, 2H), 1.55 (m, 2H), 1.26 (m, 4H), 0.84 (t, J=6.8 Hz, 3H) ppm; 13C NMR (100 MHz, DMSO-d6) δ 165.2, 146.2, 142.2, 135.1, 132.0, 130.7, 129.8, 128.3, 127.8, 127.7, 116.4, 114.7, 42.7, 35.0, 30.9, 30.5, 22.0, 14.0 ppm; UV (λmax nm) 292; IR vmax (cm−1) 3344, 2954, 1637, 1312, 811; HRMS (ESI) calcd for C23H27N5O3 [M+H]+ 422.2187, found 422.2188.

N-(4-(Decylamino)-3-nitrophenyl)-4-pentylbenzamide (4m): The title compound was synthesized from 3 following the general procedure to afford 4m as a red solid (80%). 1H NMR (300 MHz, CDCl3) δ 8.35 (brs, 1H), 8.21 (s, 1H), 7.97 (m, 1H), 7.87 (d, J=8.7 Hz, 1H), 7.80 (d, J=7.8 Hz, 2H), 7.23 (d, J=7.5, 2H), 6.79 (d, J=9.3 Hz, 1H), 3.24 (m, 2H), 2.63 (t, J=7.8 Hz, 2H), 1.68 (m, 5H), 1.27 (m, 17H), 0.88 (m, 6H) ppm; 13C NMR (100 MHz, CDCl3) δ 166.2, 147.5, 143.3, 131.7, 131.4, 130.6, 128.8, 127.3, 126.5, 118.4, 114.3, 43.3, 35.9, 32.0, 31.5, 31.0, 29.8, 29.6, 29.4 (x2), 29.1, 27.2, 22.8, 22.6, 14.2, 14.1 ppm; UV (λmax nm) 296; IR vmax (cm−1) 3370, 2920, 1649, 1520, 884; HRMS (ESI) calcd for C28H41N3O3 [M+H]+ 468.3221, found 468.3220.

N-(2-Amino-1-isbutyl-1H-benzo[d]imidazol-5-yl)-4-pentylbenzamide hydrochloride (5d): The title compound was synthesized from 4d following the general procedure to afford 5d as a white (53%). 1H δ (300 MHz, CD3OD) 7.86 (d, J=7.5 Hz, 2H), 7.59 (s, 1H), 7.30 (m, 3H), 7.15 (m, 1H), 3.82 (d, J=7.8 Hz, 2H), 2.68 (t, J=7.5 Hz, 2H), 2.23 (m, 1H), 1.67 (m, 2H), 1.36 (m, 4H), 0.95 (m, 9H) ppm; 13C NMR (100 MHz, CDCl3) δ 168.8, 151.8, 148.7, 136.8, 133.2, 130.1, 129.7, 128.7 (x2), 118.0, 111.8, 105.7, 50.6, 36.7, 32.5, 32.1, 28.9, 23.5, 19.9, 14.4 ppm; UV (λmax nm) 286; IR vmax (cm−1) 3227, 2945, 1663, 1514, 767; HRMS (ESI) calcd for C23H30N4O [M+H]+ 379.2492, found 379.2495.

N-(1-(2-(1H-Imidazol-5-yl)ethyl)-2-amino-1H-benzo[d]imidazol-5-yl)-4-pentylbenzamide dihydrochloride (5j): The title compound was synthesized from 4j following the general procedure to afford 5j as a brown solid (61%). 1H NMR (300 MHz, CD3OD) δ 7.86 (m, 3H), 7.65 (s, 1H), 7.33 (m, 2H), 7.16 (d, J=8.7 Hz, 2H) 6.83 (s, 1H), 4.29 (t, J=6.9 Hz, 2H), 3.04 (t, J=6.6 Hz, 2H), 2.68 (t, J=7.5 Hz, 2H), 1.65 (m, 2H), 1.28 (m, 4H), 0.91 (t, J=7.2 Hz, 3H) ppm; 13C NMR (100 MHz, CD3OD) δ 168.6, 151.5, 148.6, 136.9, 134.9, 133.0, 130.6, 130.0, 129.6, 128.7, 127.8, 118.9, 118.2, 111.1, 105.8, 43.2, 36.6, 32.4, 31.9, 24.1, 23.4, 14.3 ppm; UV (λmax nm) 294; IR vmax (cm−1) 3231, 2925, 1669, 1504, 805; HRMS (ESI) calcd for C24H28N6O [M+H]+ 417.2397, found 417.2398.

N-(2-Amino-1-decyl-1H-benzo[d]imidazol-5-yl)-4-pentylbenzamide hydrochloride (5m): The title compound was synthesized from 4m following the general procedure to afford 5m as a white solid (39%). 1H NMR (300 MHz, CD3OD) δ 7.85 (m, 2H), 7.60 (brs, 1H), 7.29 (m, 3H), 7.09 (m, 1H), 3.95 (m, 2H), 2.65 (t, J=6.6 Hz, 2H), 1.71 (m, 4H), 1.31 (m, 18H), 0.89 (m, 6H) ppm; 13C NMR (100 MHz, CD3OD) δ 168.8, 156.4, 148.3, 141.8, 134.0, 133.8, 132.3, 129.6, 128.6, 115.4, 109.7, 108.7, 43.3, 36.7, 33.0, 32.6, 32.1, 30.7, 30.6, 30.5, 30.4, 29.7, 27.7, 23.7, 23.6, 14.5, 14.4 ppm; UV (λmax nm) 296; IR vmax (cm−1) 3231, 2921, 1661, 1452, 801; HRMS (ESI) calcd for C29H42N4O [M+H]+ 463.3431, found 463.3434.

N-(3-Fluoro-4-nitrophenyl)-4-pentylbenzamide (7): The title compound was synthesized from 6 following the general procedure to afford 7 as a yellow solid (m.p=105° C., 98%). 1H NMR (300 MHz, CDCl3) δ 8.60 (s, 1H), 8.04 (t, J=8.7 Hz, 1H), 7.92 (m, 1H), 7.78 (d, J=7.5 Hz, 2H), 7.43 (d, J=8.4 Hz, 1H), 7.26 (d, J=8.4 Hz, 2H), 2.64 (5, J=7.5 Hz, 2H), 1.63 (m, 2H), 1.32 (m, 4H), 0.88 (t, J=6.6 Hz, 3H) ppm; 13C NMR (100 MHz, CDCl3) δ 166.4, 158.1, 155.5, 148.8, 145.3, 145.2, 130.9, 129.1, 127.4, 127.3, 127.3, 114.9, 114.9, 108.9, 35.9, 31.5, 30.9, 22.6, 14.1 ppm; IR vmax (cm−1) 3337, 2863, 1649, 1567, 1270, 866; HRMS (ESI) calcd for C11H15N3S [M+H]+ 331.1453, found 331.1451.

N-(4-Nitro-3-(butylamino)phenyl)-4-pentylbenzamide (8a): The title compound was synthesized from 7 following the general procedure to afford 8a as a yellow solid (85%). 1H NMR (400 MHz, CDCl3) δ 8.59 (s, 1H), 8.20 (s, 1H), 8.08 (d, J=9.2 Hz, 1H), 7.80 (d, J=8.0 Hz, 2H), 7.69 (s, 1H), 7.23 (d, J=8.0 Hz, 2H), 6.68 (d, J=9.6 Hz, 1H), 3.26 (m, 2H), 2.64 (m, 2H), 1.66 (m, 4H), 1.4 (m, 2H), 1.31 (m, 4H), 0.95 (m, 3H), 0.86 (m, 3H) ppm; 13C NMR (100 MHz, CDCl3) δ 166.5, 148.1, 147.3, 145.5, 131.5, 128.9, 128.2, 127.6, 127.3, 107.9, 102.4, 42.9, 35.9, 21.5, 31.0, 30.9, 22.5, 20.3, 14.0, 13.8 ppm; UV (λmax nm) 320; IR vmax (cm−1) 3293, 2952, 1676, 1391, 800; HRMS (ESI) calcd for C22H29N3O3 [M+H]+ 384.2282, found 384.2285.

N-(3-(Hexylamino)-4-nitrophenyl)-4-pentylbenzamide (8b): The title compound was synthesized from 7 following the general procedure to afford 8b as an orange solid (90%). 1H NMR (400 MHz, CDCl3) δ 8.26 (s, 1H), 8.16 (d, J=9.2 Hz, 1H), 8.00 (s, 1H), 7.79 (d, J=7.2 Hz, 2H), 7.74 (s, 1H), 7.31 (d, J=8.0 Hz, 2H), 6.54 (d, 9.2 Hz, 1H), 3.34 (m, 2H), 2.67 (t, J=7.2 Hz, 1.8 Hz, m, 2H), 1.73 (m, 2H), 1.65 (m, 2H), 1.45 (m, 2H), 1.33 (m, 8H), 0.90 (m, 6H) ppm; 13C NMR (100 MHz, CDCl3) δ 166.6, 148.0, 147.2, 145.6, 131.4, 128.8, 128.0, 127.3, 108.0, 102.4, 43.1, 35.8, 31.5, 30.8, 28.2, 26.7, 22.5, 22.4, 14.0 ppm; UV (λmax nm) 320; IR vmax (cm−1) 3295, 2955, 1678, 1395, 804; HRMS (ESI) calcd for C24H33N3O3 [M+H]+ 412.2595, found 412.2601.

N-(3-(Methylamino)-4-nitrophenyl)-4-pentylbenzamide (8c): The title compound was synthesized from 7 following the general procedure to afford 8c as a yellow solid (m.p=127° C., 100%). 1H NMR (300 MHz, CDCl3) δ 8.21 (m, 3H), 7.78 (m, 2H), 7.68 (s, 1H), 7.24 (m, 3H), 6.60 (m, 1H), 3.04 (d, J=4.5 Hz, 3H), 2.63 (t, J=4.5 Hz, 2H), 1.64 (m, 2H), 1.36 (m, 4H), 0.91 (m, 3H) ppm; 13C NMR (100 MHz, CDCl3) δ 166.6, 148.0, 147.9, 145.6, 131.3, 128.7, 128.0, 127.5, 127.3, 108.1, 102.0, 35.8, 31.4, 30.8, 29.6, 22.5, 14.0 ppm; IR vmax (cm−1) 3376, 2951, 1654, 1567, 1469, 803; HRMS (ESI) calcd for C11H15N3S [M+H]+ 342.1812, found 342.1809.

N-(3-(Ethylamino)-4-nitrophenyl)-4-pentylbenzamide (8d): The title compound was synthesized from 7 following the general procedure to afford 8d as a yellow solid (m.p=125° C., 89%). 1H NMR (300 MHz, CDCl3) δ 8.15 (m, 3H), 7.75 (m, 3H), 7.22 (m, 2H), 6.58 (m, 1H), 3.38 (m, 2H), 2.65 (m, 2H), 1.65 (m, 2H), 1.33 (m, 7H), 0.87 (m, 3H) ppm; 13C NMR (100 MHz, CDCl3) δ 166.6, 148.1, 147.0, 145.6, 131.4, 128.8, 128.1, 127.4, 127.3, 108.0, 102.4, 37.8, 35.8, 31.4, 30.8, 22.5, 14.2, 14.0 ppm; IR vmax (cm−1) 3378, 2950, 1658, 1560, 1473, 798; HRMS (ESI) calcd for C11H15N3S [M+H]+ 356.1969, found 356.1965.

N-(3-(Isopropylamino)-4-nitrophenyl)-4-pentylbenzamide (8e): The title compound was synthesized from 7 following the general procedure to afford 8e as a yellow solid (53%). 1H NMR (300 MHz, CDCl3) δ 8.59 (s, 1H), 8.20 (d, J=6.9 Hz, 1H), 8.07 (dd, J=9.3 Hz, 3.6 Hz, 1H), 7.78 (m, 3H), 7.21 (m, 2H), 6.64 (m, 1H), 3.80 (m, 1H), 2.63 (m, 2H), 1.57 (t, J=5.1 Hz, 2H), 1.27 (m, 10H), 0.85 (m, 3H) ppm; 13C NMR (100 MHz, CDCl3) δ 166.9, 147.9, 146.2, 145.7, 131.3, 128.6, 128.0, 127.3, 127.2, 108.1, 102.7, 44.0, 35.7, 31.3, 30.7, 22.4 (x2), 13.9 ppm; UV (λmax nm) 320; IR vmax (cm−1) 3295, 2955, 1678, 1395, 804; HRMS (ESI) calcd for C11H16N4S [M+H]+ 370.2125, found 370.2124.

N-(2-Amino-1-butyl-1H-benzo[d]imidazol-6-yl)-4-pentylbenzamide hydrochloride (9a): The title compound was synthesized from 8a following the general procedure to afford 9a as a brown solid (74%). 1H NMR (300 MHz, CD3OD) δ 8.03 (s, 1H), 7.88 (d, J=8.1 Hz, 2H), 7.54 (d, J=8.4 Hz, 1H), 7.33 (m, 3H), 4.11 (t, J=7.2 Hz, 2H), 2.67 (t, J=6.9 Hz, 2H), 1.78 (m, 2H), 1.65 (m, 2H), 1.44 (m, 2H), 1.32 (m, 4H), 1.00 (t, J=7.2 Hz, 3H), 0.91 (t, J=6.9 Hz, 3H) ppm; 13C NMR (100 MHz, CD3OD) δ 168.7, 141.6, 148.7, 136.4, 133.1, 131.7, 129.6, 128.7, 126.5, 118.6, 112.6, 104.4, 48.4, 43.8, 36.7, 32.5, 32.0, 31.0, 23.5, 20.9, 14.4, 14.1 ppm; UV (λmax nm) 298; IR vmax (cm−1) 3316, 2961, 1638, 1499, 1426, 763; HRMS (ESI) calcd for C23H30N4O [M+H]+ 379.2492, found 379.2497.

N-(2-Amino-1-hexyl-1H-benzo[d]imidazol-6-yl)-4-pentylbenzamide hydrochloride (9b): The title compound was synthesized from 8b following the general procedure to afford 9b as a burgundy solid (69%). 1H NMR (300 MHz, CD3OD) δ 8.01 (d, J=1.8 Hz, 1H), 7.89 (d, J=8.1 Hz, 2H), 7.58 (dd, J=8.4 Hz, 1.5 Hz, 1H), 7.33 (d, J=8.1 Hz, 1H), 7.27 (d, J=8.1 Hz, 2H), 4.05 (t, J=7.5 Hz, 2H), 2.61 (t, J=7.5, 2H), 1.70 (m, 2H), 1.35 (m, 2H), 1.29 (m, 10H), 0.83 (m, 6H) ppm; 13C NMR (100 MHz, CD3OD) δ 168.5, 151.4, 148.6, 136.4, 133.0, 131.6, 129.5, 128.7, 126.4, 118.5, 112.5, 104.2, 43.9, 36.7, 32.5 (x2), 32.0, 28.9, 27.2, 23.5 (x2), 14.4, 14.3 ppm; UV (λmax nm) 298; IR vmax (cm−1) 3312, 2960, 1643, 1497, 1432, 758; HRMS (ESI) calcd for C25H34N4O [M+H]+ 407.2805, found 407.2810.

N-(2-Amino-1-methyl-1H-benzo[d]imidazol-6-yl)-4-pentylbenzamide hydrochloride (9c): The title compound was synthesized from 8c following the general procedure to afford 9c as a white solid (m.p=232° C., 15%). 1H NMR (300 MHz, CD3OD) δ 7.86 (d, J=7.2 Hz, 2H), 7.66 (s, 1H), 7.32 (d, J=7.8 Hz, 2H), 7.17 (s, 2H), 3.53 (s, 3H), 2.67 (t, J=7.2 Hz, 2H), 1.65 (m, 2H), 1.34 (m, 4H), 0.90 (t, J=6.8 Hz, 3H) ppm; 13C NMR (100 MHz, CD3OD) δ 168.8, 157.0, 148.4, 139.5, 135.6, 133.8, 132.4, 129.6, 128.6, 116.8, 115.3, 103.2, 36.7, 32.6, 32.2, 28.8, 23.6, 14.4 ppm; IR vmax (cm−1) 3295, 2955, 1678, 1510, 1454, 732; HRMS (ESI) calcd for C11H15N3S [M+H]+ 337.2023, found 337.2023.

N-(2-Amino-1-ethyl-1H-benzo[d]imidazol-6-yl)-4-pentylbenzamide hydrochloride (9d): The title compound was synthesized from 8d following the general procedure to afford 9d as a whitepink solid (m.p=234° C., 30%). 1H NMR (400 MHz, CD3OD) δ 7.98 (s, 1H), 7.87 (d, J=8.0 Hz, 2H), 7.55 (d, J=8.8 Hz, 1H), 7.29 (m, 3H), 4.13 (q, J=7.2 Hz, 2H), 2.61 (t, J=7.6 Hz, 2H), 1.59 (m, 2H), 1.36 (t, J=7.2 Hz, 3H), 1.30 (m, 4H), 0.89 (t, J=6.4 Hz, 3H) ppm; 13C NMR (100 MHz, CD3OD) δ 168.4, 151.4, 148.5, 136.4, 133.0, 131.1, 129.5, 128.7, 126.5, 118.6, 112.5, 104.1, 38.9, 36.7, 32.5, 32.0, 23.5, 14.4, 13.4 ppm; IR vmax (cm−1) 3299, 2940, 1659, 1540, 1470, 750; HRMS (ESI) calcd for C11H15N3S [M+H]+ 351.2179, found 351.2181.

N-(2-Amino-1-isopropyl-1H-benzo[d]imidazol-6-yl)-4-pentylbenzamide hydrochloride (9e): The title compound was synthesized from 8e following the general procedure to afford 9e as a red solid(m.p=252° C., 20%). 1H NMR (400 MHz, CD3OD) δ 8.29 (s, 1H), 7.89 (d, J=7.6 Hz, 2H), 7.56 (d, J=8.4 Hz, 1H), 7.36 (m, 3H), 4.77 (m, J=6.4 Hz, 1H), 2.68 (t, J=7.2 Hz, 2H), 1.67 (m, 8H), 1.33 (m, 4H), 0.90 (t, J=6.8 Hz, 3H) ppm; 13C NMR (100 MHz, CD3OD) δ 168.9, 151.1, 148.7, 136.1, 133.3, 130.1, 129.7, 128.7, 127.1, 118.4, 112.7, 106.5, 36.7, 32.6, 32.1, 23.5, 20.2, 14.4 ppm; IR vmax (cm−1) 3315, 2963, 1640, 1497, 1432, 763; HRMS (ESI) calcd for C11H15N3S [M+H]+ 365.2336, found 365.2338.

2-Amino-N-(3,4-dichlorophenyl)-1-(3-phenylpropyl)-1H-benzo[d]imidazole-5-carboxamide hydrochloride (15): The title compound was synthesized from 14 following the general procedure to afford 15 as a white solid (40%). 1H NMR (400 MHz, CD3OD) δ 8.01 (s, 1H), 7.92 (m, 2H), 7.60 (m, 1H), 7.43 (m, 2H), 7.25 (m, 2H), 7.17 (m, 3H), 4.23 (t, J=6.6 Hz, 2H), 2.75 (t, J=7.4 Hz, 2H), 2.15 (t, J=6.8 Hz, 2H) ppm; 13C NMR (175 MHz, CD3OD) δ 167.2, 152.3, 141.7, 139.8, 134.3, 133.0, 131.5, 131.3, 130.1, 129.5, 129.2, 127.8, 127.2, 124.6, 123.1, 121.4, 112.5, 111.0, 43.9, 33.5, 30.3 ppm; UV (λmax nm) 298; IR vmax (cm−1) 3303, 1567, 1472, 1214, 856, 700; HRMS (ESI) calcd for C23H20Cl2N4O [M+H]+ 439.1087, found 439.1096.

Allyl tert-Butyl (1-(3-phenylpropyl)-1H-benzo[d]imidazole-2,5-diyl)dicarbamate (19): The title compound was synthesized from 18 following the general procedure to afford 19 as a brown oil (25%). 1H NMR (300 MHz, CD3OD) δ 7.62 (brs, 1H), 7.19 (m, 2H), 7.11 (m, 3H), 6.97 (d, J=8.8 Hz, 2H), 6.00 (m, 1H), 5.36 (m, 1H), 5.18 (m, 1H), 4.61 (m, 2H), 3.35 (t, J=7.6 Hz, 2H), 2.57 (t, J=7.6 Hz, 2H), 1.95 (t, J=7.2 Hz, 2H), 1.49 (s, 9H) ppm; 13C NMR (100 MHz, CD3OD) δ 163.6, 155.2, 154.3, 142.3, 136.3, 134.9, 129.9, 129.3 (x2), 126.9, 126.6, 117.4, 115.5, 110.2, 103.6, 80.7, 67.1, 42.5, 33.7, 30.9, 28.7 ppm; UV (λmax nm) 312; IR vmax (cm−1) 2929, 1710, 1499, 1364, 1150, 1052, 700; HRMS (ESI) calcd for C25H30N4O4 [M+H]+ 451.2340, found 451.2351.

1-(2-Amino-1-(3-phenylpropyl)-1H-benzo[d]imidazol-5-yl)-3-(3,4-dichlorophenyl)urea hydrochloride (19): The title compound was synthesized from 19 following the general procedure to afford 20 as a brown solid (20%). 1H NMR (300 MHz, CD3OD) δ 7.72 (m, 2H), 7.31 (m, 4H), 7.17 (m, 5H), 4.08 (t, J=7.4 Hz, 2H), 2.71 (t, J=7.8 Hz, 2H), 2.08 (t, J=7.2 Hz, 2H) ppm; 13C NMR (175 MHz, CD3OD) δ 154.5, 151.2, 141.8, 140.6, 137.3, 133.1, 131.3, 130.4, 129.5, 129.2, 127.2, 127.0, 125.9, 121.1, 119.3, 116.2, 111.2, 103.7, 43.5, 33.6, 30.4 ppm; UV (λmax nm) 298; IR vmax (cm−1) 2918, 1638, 1583, 1301, 1023, 813; HRMS (ESI) calcd for C23H21Cl2N5O [M+H]+ 454.1196, found 454.1203.

Conclusions

After the identification of 2-ABI compound 1 as a *S. typhimurium* biofilm inhibitor, probing of the SAR of the 2-ABIs elucidated six new analogues with $IC_{50}$ values of less than 10 μM. Utilizing the same para-pentyl benzoyl tail as the parent compound 1, structural modifications to the head of the 2-ABIs in the para position to the amide yielded compounds 5a and 5b with $IC_{50}$ values of 6.66±0.32 and 9.59±0.23 μM respectively. Modification of the tail region yielded compounds 15a (5.22±0.11 μM), 15b (5.38±0.79 μM), 15c (5.58±0.21 μM), and 15d (6.3±1.29 μM) that displayed improved activity. Modification of the linker between the head and the tail yielded the urea compound 20 with a comparable IC50 (7.69±0.25 μM) to that of the amide parent compound, 10d (6.30±1.29 μM). Substitution the 2-ABI head at the meta position to the amide (9a-e) and reversal of the amide moiety (15) did not produce an increase in activity. Compounds 10a and 20 were then shown to be non-toxic to planktonic bacterial growth at their $IC_{50}$ values, demonstrating that they show specific anti-*S. typhimurium* biofilm inhibitory activity. Additionally, compounds 10d and 10e and other related 2-ABIs17 displayed no toxicity to *G. mellonella* at 400 mg kg$^{-1}$ (ESI†), thus making them potential candidates for future in vivo studies.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

The invention claimed is:

1. A method for inhibiting biofilm formation or dispersing a biofilm in a subject comprising the step of administering to the subject a pharmaceutical composition comprising a therapeutically effective amount of a compound having a structure represented by a formula:

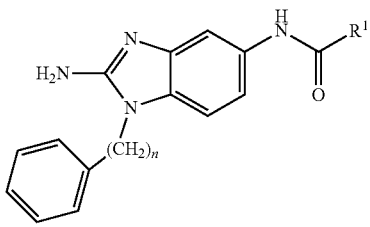

wherein $R^1$ is a structure represented by a formula:

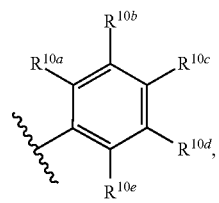

wherein each of $R^{10a}$, $R^{10b}$, $R^{10c}$, $R^{10d}$, and $R^{10e}$ is independently selected from hydrogen, halogen, C1-C6 alkyl, C1-C6 alkoxy, and C1-C6 haloalkyl, provided that at least one of $R^{10a}$, $R^{10b}$, $R^{10c}$, $R^{10d}$, and $R^{10e}$ is not hydrogen; and n is an integer selected from 1, 2, 3, 4, 5, 6, 7, 8, 9, 10, 11, and 12, or a pharmaceutically acceptable salt thereof; and a pharmaceutically acceptable carrier.

2. The method of claim 1, wherein each of $R^{10a}$, $R^{10b}$, $R^{10c}$, $R^{10d}$, and $R^{10e}$ is independently selected from hydrogen, halogen, C1-C6 alkyl, and C1-C6 alkoxy, provided that two $R^{10a}$, $R^{10b}$, $R^{10c}$, $R^{10d}$, and $R^{10e}$ are hydrogen.

3. The method of claim 1, wherein each of $R^{10a}$, $R^{10b}$, $R^{10c}$, $R^{10d}$, and $R^{10e}$ is independently selected from hydrogen, bromo, chloro, fluoro, C1-C3 alkyl, and C1-C3 alkoxy, provided that at least one of $R^{10a}$, $R^{10b}$, $R^{10c}$, $R^{10d}$, and $R^{10e}$ is not hydrogen.

4. The method of claim 1, wherein each of $R^{10a}$, $R^{10b}$, $R^{10c}$, $R^{10d}$, and $R^{10e}$ is independently selected from hydrogen, bromo, chloro, C1-C3 alkyl, and C1-C3 alkoxy, provided that at least one of $R^{10a}$, $R^{10b}$, $R^{10c}$, $R^{10d}$, and $R^{10e}$ is not hydrogen.

5. The method of claim 1, wherein each of $R^{10a}$, $R^{10b}$, $R^{10c}$, $R^{10d}$, and $R^{10e}$ is independently selected from hydrogen, bromo, and chloro, provided that at least one of $R^{10a}$, $R^{10b}$, $R^{10c}$, $R^{10d}$, and $R^{10e}$ is not hydrogen.

6. The method of claim 1, wherein each of $R^{10a}$, $R^{10b}$, $R^{10c}$, $R^{10d}$, and $R^{10e}$ is independently selected from hydrogen, bromo, and chloro, provided that two of $R^{10a}$, $R^{10b}$, $R^{10c}$, $R^{10d}$, and $R^{10e}$ are hydrogen.

7. The method of claim 1, wherein each of $R^{10a}$, $R^{10b}$, $R^{10c}$, $R^{10d}$, and $R^{10e}$ is independently selected from hydrogen, bromo, and chloro, provided that three of $R^{10a}$, $R^{10b}$, $R^{10c}$, $R^{10d}$, and $R^{10e}$ are hydrogen.

8. The method of claim 1, wherein each of $R^{10a}$, $R^{10b}$, $R^{10c}$, $R^{10d}$, and $R^{10e}$ is independently selected from hydrogen, bromo, and chloro, provided that four of $R^{10a}$, $R^{10b}$, $R^{10c}$, $R^{10d}$, and $R^{10e}$ are hydrogen.

9. The method of claim 1, wherein $R^1$ is a structure represented by a formula:

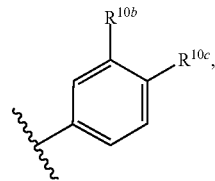

wherein each of $R^{10b}$ and $R^{10c}$ is independently selected from halogen, C1-C6 alkyl, C1-C6 alkoxy, and C1-C6 haloalkyl.

10. The method of claim 1, wherein $R^1$ is a structure represented by a formula:

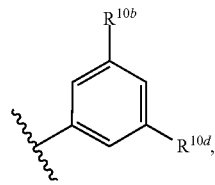

wherein each of $R^{10b}$ and $R^{10d}$ is independently selected from halogen, C1-C6 alkyl, C1-C6 alkoxy, and C1-C6 haloalkyl.

11. The method of claim 1, wherein $R^1$ is a structure represented by a formula:

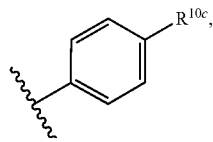

wherein $R^{10c}$ is selected from halogen, C1-C6 alkyl, C1-C6 alkoxy, and C1-C6 haloalkyl.

12. The method of claim 1, wherein the compound is

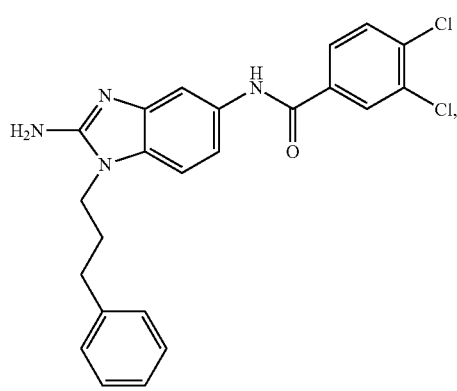

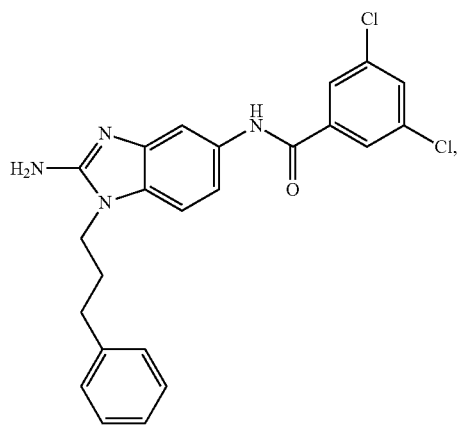

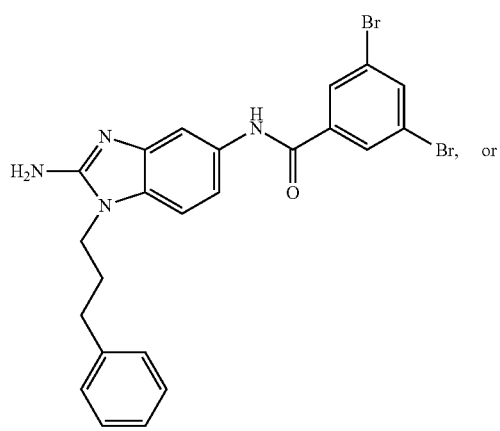

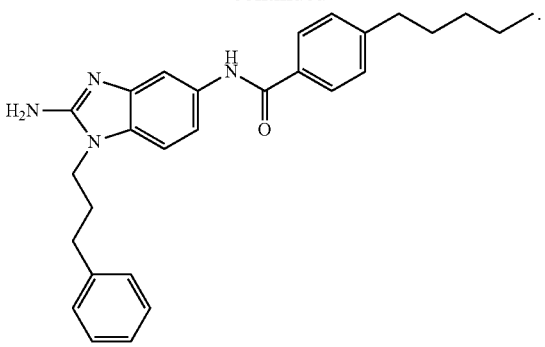

13. A method for inhibiting biofilm formation or dispersing a biofilm in a subject, wherein the subject has a *Salmonella enterica* infection, comprising the step of administering to the subject a pharmaceutical composition comprising a therapeutically effective amount of a compound having a structure represented by a formula:

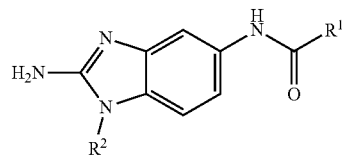

wherein $R^1$ is selected from a C1-C12 alkyl, a C3-C12 cycloalkyl; and a substituted aryl; and
wherein $R^2$ is selected from a C1-C12 alkyl, a C3-C12 cycloalkyl; and a substituted aryl;
or a pharmaceutically acceptable salt thereof; and a pharmaceutically acceptable carrier.

14. The method of claim 13, wherein $R^1$ is selected from a C1-C12 alkyl and a substituted aryl.

15. The method of claim 13, wherein $R^1$ is a substituted aryl.

16. The method of claim 13, wherein $R^1$ is a structure represented by a formula:

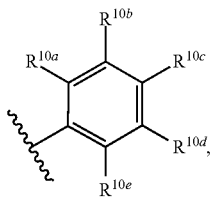

wherein each of $R^{10a}$, $R^{10b}$, $R^{10c}$, $R^{10d}$, and $R^{10e}$ is independently selected from hydrogen, halogen, C1-C6 alkyl, C1-C6 alkoxy, and C1-C6 haloalkyl, provided that at least one of $R^{10a}$, $R^{10b}$, $R^{10c}$, $R^{10d}$, and $R^{10e}$ is not hydrogen.

17. The method of claim 16, wherein
each of $R^{10a}$, $R^{10b}$, $R^{10c}$, $R^{10d}$, and $R^{10e}$ is independently selected from hydrogen, halogen, C1-C6 alkyl, and C1-C6 alkoxy, provided that two $R^{10a}$, $R^{10b}$, $R^{10c}$, $R^{10d}$, and $R^{10e}$ are hydrogen; or
each of $R^{10a}$, $R^{10b}$, $R^{10c}$, $R^{10d}$, and $R^{10e}$ is independently selected from hydrogen, bromo, chloro, fluoro, C1-C3 alkyl, and C1-C3 alkoxy, provided that at least one of $R^{10a}$, $R^{10b}$, $R^{10c}$, $R^{10d}$, and $R^{10e}$ is not hydrogen; or each of $R^{10a}$, $R^{10b}$, $R^{10c}$, $R^{10d}$, and $R^{10e}$ is independently selected from hydrogen, bromo, chloro, C1-C3 alkyl, and C1-C3 alkoxy, provided that at least one of $R^{10a}$, $R^{10b}$, $R^{10c}$, $R^{10d}$, and $R^{10e}$ is not hydrogen; or each of $R^{10a}$, $R^{10b}$, $R^{10c}$, $R^{10d}$, and $R^{10e}$ is independently selected from hydrogen, bromo, and chloro, provided that at least one of $R^{10a}$, $R^{10b}$, $R^{10c}$, $R^{10d}$, and $R^{10e}$ is not hydrogen; or each of $R^{10a}$, $R^{10b}$, $R^{10c}$, $R^{10d}$, and $R^{10e}$ is independently selected from hydrogen, bromo, and chloro, provided that two of $R^{10a}$, $R^{10b}$, $R^{10c}$, $R^{10d}$, and $R^{10e}$ are hydrogen; or each of $R^{10a}$, $R^{10b}$, $R^{10c}$, $R^{10d}$, and $R^{10e}$ is independently selected from hydrogen, bromo, and chloro, provided that three of $R^{10a}$, $R^{10b}$, $R^{10c}$, $R^{10d}$, and $R^{10e}$ are hydrogen; or each of $R^{10a}$, $R^{10b}$, $R^{10c}$, $R^{10d}$, and $R^{10e}$ is independently selected from hydrogen, bromo, and chloro, provided that four of $R^{10a}$, $R^{10b}$, $R^{10c}$, $R^{10d}$, and $R^{10e}$ are hydrogen.

18. The method of claim 13, wherein $R^1$ is a structure represented by a formula:

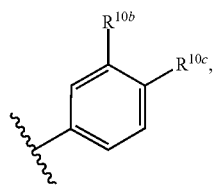

wherein each of $R^{10b}$ and $R^{10c}$ is independently selected from halogen, C1-C6 alkyl, C1-C6 alkoxy, and C1-C6 haloalkyl.

19. The method of claim 13, wherein $R^1$ is a structure represented by a formula:

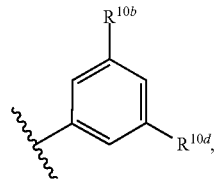

wherein each of $R^{10b}$ and $R^{10d}$ is independently selected from halogen, C1-C6 alkyl, C1-C6 alkoxy, and C1-C6 haloalkyl.

20. The method of claim 13, wherein $R^1$ is a structure represented by a formula:

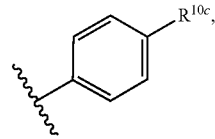

wherein $R^{10c}$ is selected from halogen, C1-C6 alkyl, C1-C6 alkoxy, and C1-C6 haloalkyl.

* * * * *